(12) United States Patent
Garamszegi

(10) Patent No.: US 10,433,875 B2
(45) Date of Patent: Oct. 8, 2019

(54) FIXATION SCREW ASSEMBLY

(71) Applicant: Phygen, LLC, Irvine, CA (US)

(72) Inventor: Laszlo Garamszegi, Mission Viejo, CA (US)

(73) Assignee: Phygen, LLC, Irvine, CA (US)

(*) Notice: Subject to any disclaimer, the term of this patent is extended or adjusted under 35 U.S.C. 154(b) by 126 days.

(21) Appl. No.: 15/333,012

(22) Filed: Oct. 24, 2016

(65) Prior Publication Data

US 2017/0135729 A1    May 18, 2017

Related U.S. Application Data

(63) Continuation of application No. 13/274,243, filed on Oct. 14, 2011, now Pat. No. 9,510,867.

(60) Provisional application No. 61/393,835, filed on Oct. 15, 2010.

(51) Int. Cl.
*A61B 17/70* (2006.01)
*A61B 17/80* (2006.01)
*A61B 90/00* (2016.01)

(52) U.S. Cl.
CPC ...... *A61B 17/7032* (2013.01); *A61B 17/7037* (2013.01); *A61B 17/7059* (2013.01); *A61B 17/8052* (2013.01); *A61B 17/7049* (2013.01); *A61B 2090/037* (2016.02)

(58) Field of Classification Search
CPC ............ A61B 17/8052; A61B 17/7032; A61B 17/7037
See application file for complete search history.

(56) References Cited

U.S. PATENT DOCUMENTS

| | | | |
|---|---|---|---|
| 3,259,161 | A | 7/1966 | Rosan |
| 4,568,228 | A | 2/1986 | Rosan, Jr. |
| 5,275,601 | A | 1/1994 | Gogolewski et al. |
| 5,667,508 | A | 9/1997 | Errico et al. |
| 5,752,957 | A | 5/1998 | Ralph et al. |
| 5,882,350 | A | 3/1999 | Ralph et al. |
| 6,227,782 | B1 | 5/2001 | Bowling et al. |
| 6,302,888 | B1 | 10/2001 | Mellinger et al. |
| 6,331,179 | B1 | 12/2001 | Freid et al. |
| 6,361,537 | B1 | 3/2002 | Anderson |
| 6,440,137 | B1 | 8/2002 | Horvath et al. |
| 6,726,689 | B2 | 4/2004 | Jackson |

(Continued)

FOREIGN PATENT DOCUMENTS

WO    WO-2012051576 A2    4/2012

OTHER PUBLICATIONS

PCT/US2011/056435 International Preliminary Report on Patentability dated Apr. 16, 2013.

(Continued)

*Primary Examiner* — Jacqueline T Johanas
(74) *Attorney, Agent, or Firm* — Wilson Sonsini Goodrich & Rosati

(57) ABSTRACT

An orthopedic device has a configuration that employs a scalloped profile that defines internal scalloped edges having troughs and crests that extend substantially along the outer edge of a head of the device. The troughs and crests interface with a series of troughs and crests around the openings in the device. Each of the openings includes an outwardly extending slot that permits the opening to expand and contract outward as the head of the anchor is rotated. This enables an anti-backout feature that prevents or substantially inhibits undesired rotation and backout.

12 Claims, 30 Drawing Sheets

(56) References Cited

U.S. PATENT DOCUMENTS

| | | |
|---|---|---|
| 6,755,829 B1 | 6/2004 | Bono et al. |
| 7,081,117 B2 | 7/2006 | Bono et al. |
| 7,229,442 B2 | 6/2007 | Schafer |
| 7,261,506 B2 | 8/2007 | Smolarek |
| 7,335,202 B2 | 2/2008 | Matthis et al. |
| 7,641,429 B2 | 1/2010 | Distasio et al. |
| 7,670,072 B2 | 3/2010 | Tella et al. |
| 7,699,880 B2 | 4/2010 | Orbay et al. |
| 7,935,137 B2 | 5/2011 | Gorhan et al. |
| 7,942,913 B2 | 5/2011 | Ziolo et al. |
| 7,955,362 B2 | 6/2011 | Erickson et al. |
| 7,963,982 B2 | 6/2011 | Kirschman |
| 8,075,590 B2 | 12/2011 | Janowski et al. |
| 8,162,990 B2 | 4/2012 | Potash et al. |
| 8,216,284 B2 | 7/2012 | Leung |
| 8,262,662 B2 | 9/2012 | Beardsley et al. |
| 8,328,856 B1 | 12/2012 | Donahoe et al. |
| 8,496,693 B2 | 7/2013 | Robinson |
| 9,510,867 B2 | 12/2016 | Garamszegi et al. |
| 2002/0045898 A1 | 4/2002 | Freid et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2005/0096657 A1 | 5/2005 | Autericque et al. |
| 2005/0177154 A1 | 8/2005 | Moumene et al. |
| 2005/0192572 A1 | 9/2005 | Abdelgany et al. |
| 2006/0129149 A1 | 6/2006 | Iott et al. |
| 2006/0142766 A1 | 6/2006 | Schafer |
| 2007/0055235 A1 | 3/2007 | Janowski et al. |
| 2007/0233062 A1 | 10/2007 | Berry |
| 2008/0045953 A1 | 2/2008 | Garamszegi |
| 2008/0097444 A1 | 4/2008 | Erickson et al. |
| 2008/0119849 A1 | 5/2008 | Beardsley et al. |
| 2008/0262548 A1 | 10/2008 | Lange et al. |
| 2008/0269809 A1 | 10/2008 | Garamszegi et al. |
| 2008/0287998 A1 | 11/2008 | Doubler et al. |
| 2009/0024161 A1 | 1/2009 | Bonutti et al. |
| 2010/0125302 A1 | 5/2010 | Hammill, Sr. et al. |
| 2010/0137920 A1 | 6/2010 | Hammill, Sr. et al. |
| 2010/0160977 A1 | 6/2010 | Gephart et al. |
| 2011/0270325 A1 | 11/2011 | Keyer et al. |
| 2012/0095513 A1 | 4/2012 | Humphreys |
| 2012/0150239 A1 | 6/2012 | Garamszegi et al. |
| 2012/0158059 A1 | 6/2012 | Freid et al. |
| 2012/0221054 A1 | 8/2012 | Jackson |
| 2012/0253409 A1 | 10/2012 | Peterson et al. |
| 2013/0018428 A1 | 1/2013 | Harper et al. |

OTHER PUBLICATIONS

PCT/US2011/056435 International Search Report dated May 29, 2012.
PCT/US2011/056435 Written Opinion dated May 29, 2012.
U.S. Appl. No. 13/274,243 Office Action dated Aug. 20, 2015.
U.S. Appl. No. 13/274,243 Office Action dated Dec. 9, 2015.
U.S. Appl. No. 13/274,243 Office Action dated Feb. 6, 2015.
U.S. Appl. No. 13/274,243 Office Action dated May 15, 2014.
U.S. Appl. No. 13/274,243 Office Action dated May 3, 2013.
U.S. Appl. No. 13/274,243 Office Action dated Sep. 18, 2013.

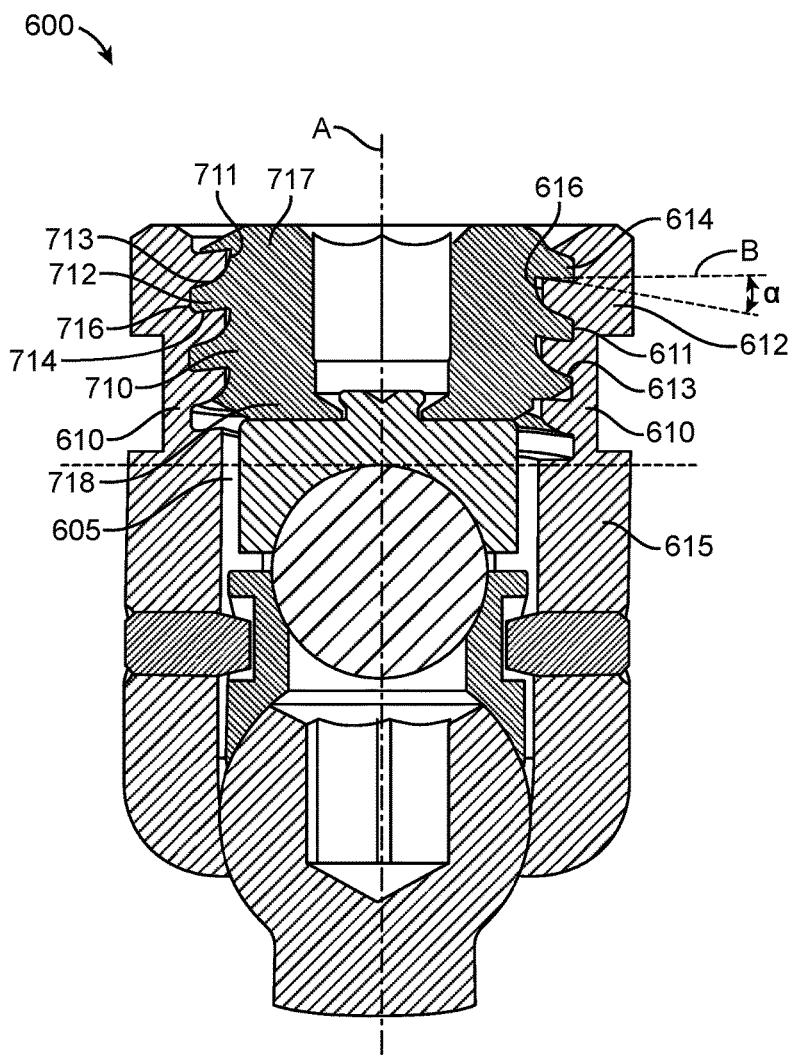
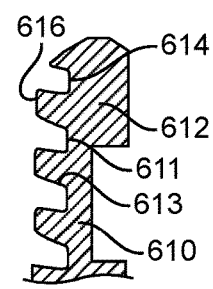
FIG. 15B
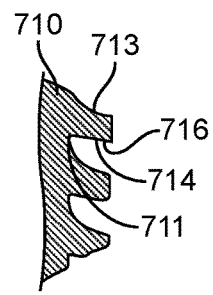
FIG. 15C
FIG. 15A

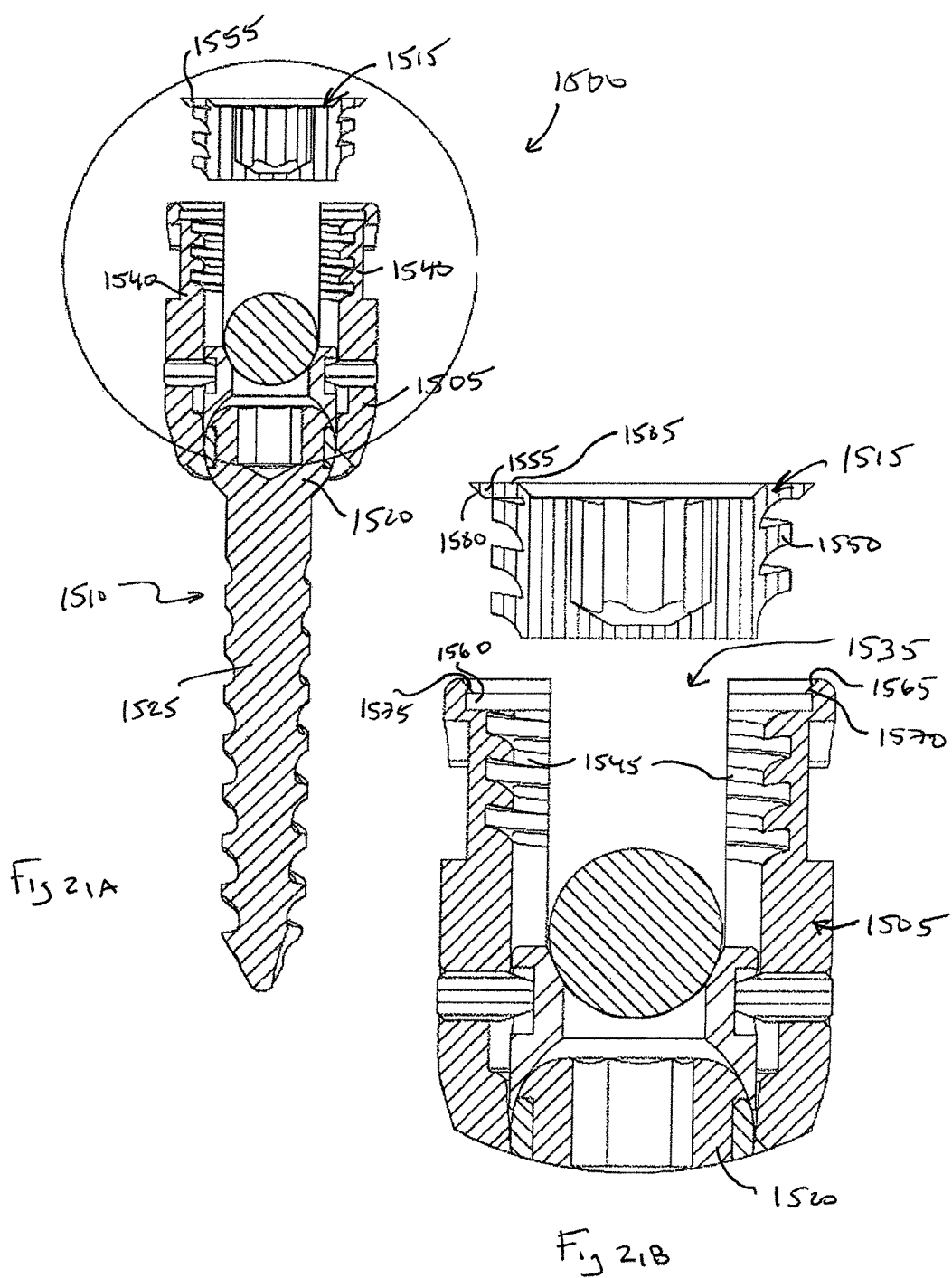

FIXATION SCREW ASSEMBLY

REFERENCE TO PRIORITY DOCUMENT

This application is a continuation of U.S. patent application Ser. No. 13/274,243, filed Oct. 14, 2011, entitled "FIXATION SCREW ASSEMBLY", which claims priority of U.S. Provisional Patent Application Ser. No. 61/393,835 entitled FIXATION SCREW ASSEMBLY and filed on Oct. 15, 2010. The disclosure of each referenced Patent Application is hereby incorporated by reference in its entirety.

BACKGROUND AND SUMMARY

The present disclosure relates to orthopedic implants and, in particular, relates to spinal implants.

Described herein are embodiments and methods for securing a bone stabilizer assembly. Some embodiments provide a coupling member assembly, for securing a pedicle screw to a retention rod, the assembly including a coupling member having two opposed threaded internal surfaces and a locking member first portion and a compression nut configured to be received by the coupling member and to threadingly engage the coupling member threaded internal surfaces, the compression nut having a locking member second portion. In some embodiments, the coupling member and the compression nut are configured to engage each other via the locking member first and second portions such that relative rotation between the coupling member and compression nut is limited without deflection of the opposed threaded internal surfaces relative to each other.

In some embodiments, the locking member first portion comprises a recess in the internal bore, the recess having a greater cross-sectional dimension than a greatest cross-sectional dimension of the threaded internal surfaces. Some embodiments provide that the locking member first portion comprises a lip having a cross-sectional dimension less than the cross-sectional dimension of the recess, and the locking member second portion is configured to engage the lip and thereby deflect the two opposed threaded internal surfaces relative to each other as the compression nut is received by the coupling member.

In some embodiments, the locking member second portion comprises a flange on the compression nut, the flange having a greater cross-sectional dimension than a greatest cross-section dimension of the threaded internal surfaces of the coupling member. In some embodiments, the locking member first portion comprises a lip that interlocks with a portion of the flange to prevent withdrawal of the compression nut from the coupling member.

Some embodiments provide that the locking member first and second portions comprise sawtooth edges that interlock to limit relative rotational movement between the compression nut and the coupling member without deflection of the two opposed threaded internal surfaces. In some embodiments, the locking member first and second portions comprise a plurality of detents that limit relative rotation between the compression nut and the coupling member.

In some embodiments, the locking member first portion comprises a tapered surface that is configured to deflect the two opposed threaded internal surfaces by engagement with a portion of the compression nut as the compression nut is received by the coupling member. Some embodiments provide that the locking member second portion comprises a tapered surface that is configured to deflect the two opposed threaded internal surfaces by engagement with a portion of the coupling member as the compression nut is received by the coupling member.

Some methods include providing a fixation member configured to engage a bone and having a head portion and shank portion. Some methods also include providing a coupling member having an internal bore sized to receive the shank portion of the fixation element and a seat configured to support the head portion of the fixation element, the coupling member further adapted to receive a stabilizer rod, the internal bore having two opposed threaded internal surfaces and a locking member first portion. In some methods, a compression nut is provided that is configured to be rotatingly received by the coupling member and to threadingly engage the coupling member threaded internal surfaces, the compression nut having a locking member second portion, the compression nut configured to translate a force to the head portion through the rod such that the head portion is forced against the seat of the coupling member to limit relative movement between the fixation element and the coupling member. Some methods include engaging the coupling member and the compression nut via the locking member first and second portions such that relative rotation between the coupling member and compression nut is limited without deflection of the opposed threaded internal surfaces relative to each other.

Some methods further include deflecting the opposed threaded internal surfaces relative to each other by threadingly engaging the compression nut with the coupling member. In some methods the opposed threaded internal surfaces are deflected from each other a distance less than a height of threads along the threaded internal surfaces.

Disclosed are bone stabilization assemblies for use in skeletal systems. In one aspect, a bone stabilizer assembly includes a fixation element, a coupling element, a saddle, a compression nut, and retention means for retaining the saddle in the coupling element in a floating configuration that permits a predetermined amount of movement between the saddle and the coupling element. The fixation element is adapted to engage a bone and has a head portion and shank portion. The coupling element has an internal bore sized to receive the shank portion of the fixation element and a seat adapted to support the head portion of the fixation element. The coupling element is also adapted to receive a stabilizer rod. The saddle is movably mounted in the coupling element below the stabilizer rod when the stabilizer rod is in the coupling element. The compression nut is engagable with the coupling element. The compression nut is adapted to rotatingly move distally into the coupling element to translate a force to the head portion through the rod and the saddle such that the head portion is forced against the seat of the coupling element to prevent relative movement between the fixation element and the coupling element.

In another aspect, a bone stabilizer assembly includes a fixation element, a coupling element, and a saddle. The fixation element is adapted to engage a bone and has a head portion and shank portion. The coupling element has an internal bore sized to receive the shank portion of the fixation element and a seat adapted to support the head portion of the fixation element. The coupling element further includes a pair of opposed walls separated by a stabilizer rod-receiving channel. Inner surfaces of the opposed walls include inner threads for mating with a compression nut and opposing indentations located below the inner threads. The saddle is movably mounted in the coupling element below the stabilizer rod when the stabilizer rod is in the coupling element. The saddle includes a pair of opposed walls separated by a rod-receiving region. Outer surfaces of the opposed walls include opposing protrusions that extend laterally from the walls. The protrusions are adapted to engage the opposing indentations in the opposed walls of the coupling element so as to retain the saddle within the coupling element when the stabilizer rod is disengaged from the coupling element.

In another aspect, a bone stabilizer assembly includes a coupling element and a compression nut. The coupling element includes a plurality of wall sections defining a longitudinal bore. The coupling element also includes a transverse channel substantially perpendicular to the bore. The compression nut includes a substantially cylindrical engagement portion having a longitudinal axis. A thread is formed on the engagement portion so that the engagement portion is adapted to be threadedly engaged within the bore to the wall sections. The thread has a profile that has a rotation stiffening component and an anti-splay component. The rotation stiffening component and the anti-splay component are integrated.

In another aspect, a bone stabilizer assembly includes a coupling element, and a compression nut. The coupling element includes a plurality of wall sections defining a longitudinal bore and a transverse channel substantially perpendicular to the bore. The compression nut includes a substantially cylindrical engagement portion having a longitudinal axis and a thread formed on the engagement portion so that the engagement portion is adapted to be threadedly engaged within the bore to the wall sections. The thread is sloped in a distal direction from a root of the thread to a crest of the thread.

The details of one or more embodiments are set forth in the accompanying drawings and the description below. Other features, objects, and advantages will be apparent from the description and drawings, and from the claims.

BRIEF DESCRIPTION OF THE DRAWINGS

A general architecture that implements various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

FIG. 5a shows a cross-sectional view of a bone fixation assembly according to another embodiment.

FIG. 5b is a magnified view of region 5b depicted in FIG. 5a.

FIG. 8b is a magnified view of region 8b depicted in FIG. 8a.

FIG. 12b is a magnified view of region 12b depicted in FIG. 12a.

FIG. 13b is a magnified view of region 13b depicted in FIG. 13a.

FIG. 14b is a perspective view of the saddle depicted in FIG. 14a.

FIG. 15a is a cross-sectional view of a bone fixation assembly according to another embodiment.

FIG. 15b is a cross-sectional view of the external threads of the compression nut depicted in FIG. 15a.

FIG. 15c is a cross-sectional view of the internal threads of the coupling element depicted in FIG. 15a.

FIG. 17b is a cross-sectional view of the external threads of the compression nut depicted in FIG. 17a.

FIG. 17c is a cross-sectional view of the internal threads of the coupling element depicted in FIG. 17a.

FIG. 18b is a cross-sectional view of the compression nut and top saddle depicted in FIG. 18a.

FIG. 19b is a cross-sectional view of the compression nut and top saddle depicted in FIG. 19a.

FIG. 21A is a cross-sectional exploded view of embodiments of an anchor assembly described herein.

FIG. 21B is a cross sectional exploded view of the anchor assembly depicted in FIG. 21A.

DETAILED DESCRIPTION

Before discussing the embodiments in detail, it may be helpful to first briefly review the basic devices and concepts used in orthopedic surgery, and particularly spine surgery. Bone stabilization assemblies are commonly used throughout the skeletal system to stabilize broken, fractured, diseased or deformed bones. In particular, pedicle screw systems are particularly well adapted for the fixation and manipulation of the bones of the vertebral column.

Figure 1A:
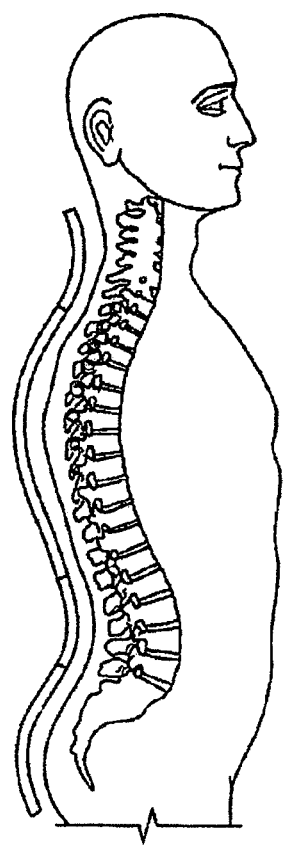
FIG. 1a is an illustration of a human vertebral column.
Figure 1B:
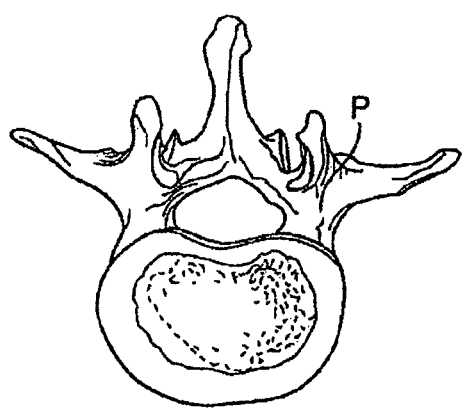
FIG. 1b is a superior view of a typical human vertebra.
Figure 1C:
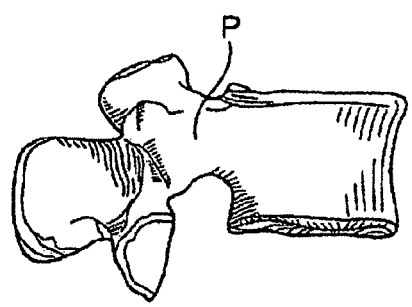
FIG. 1c is a lateral view of the vertebra depicted in FIG. 1b.

A vertebral pedicle is a dense stem-like structure that projects from the posterior of a vertebra. There are two pedicles per vertebra that connect to other structures (e.g. lamina, vertebral arch). The location of a pedicle P is illustrated in FIGS. 1b and 1c, which illustrate a typical vertebral column, a superior view of a typical vertebra, and a lateral view of a typical vertebra, respectively.

Bone screws have been used in spinal instrumentation since the 1960s. A pedicle screw is a particular type of bone screw designed for implantation into a vertebral pedicle. Monoaxial pedicle screws are still used quite often, but the current standard for implantation is a polyaxial pedicle screw made of titanium or titanium alloy. Titanium alloy is useful, because it is highly resistant to corrosion and fatigue, and is MRI compatible. The screw is threaded and the head is moveable, allowing it to swivel so as to defray vertebral stress. Polyaxial pedicle screw lengths range from about 30 mm to about 60 mm with diameters ranging from about 5.0 mm to about 8.5 mm.

Figure 2:
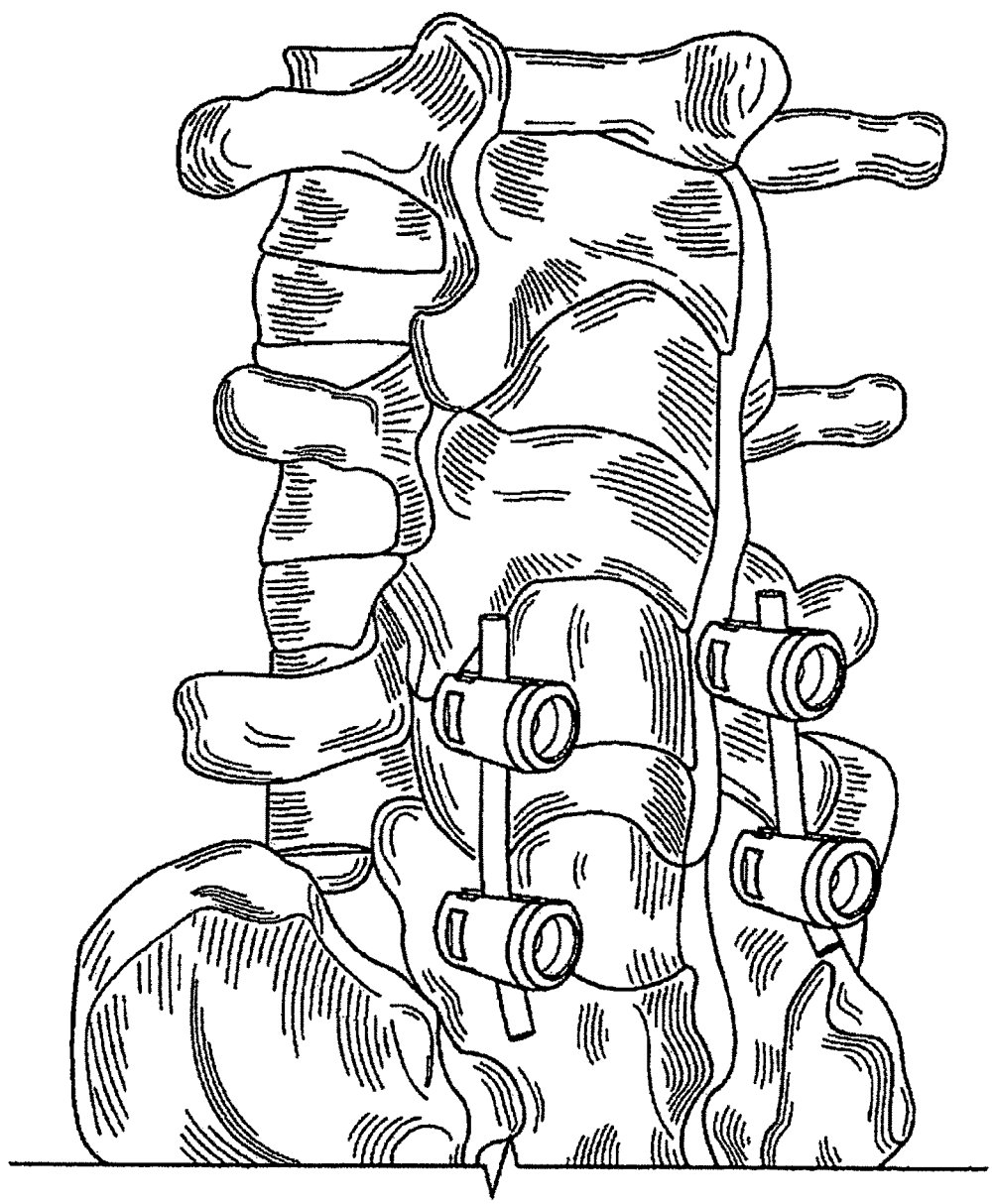
FIG. 2 is an illustration of a set of pedicle screws implanted into a human vertebral column

Pedicle screws are used to correct deformity, and or to treat trauma. They can be used in instrumentation procedures to affix rods and plates to the spine. They can also be used to immobilize part of the spine to assist fusion by holding bony structures together. Although pedicle screws are most often used in the lumbar (lumbosacral) spine, they can be implanted in the thoracic and sacral vertebra. The surgeon uses fluoroscopy, conventional x-ray, and sometimes computer-assisted visualization to determine the depth and angle for screw placement. A receiving channel is drilled and the screw is inserted. The screws themselves do not fixate the spinal segment, but act as firm anchor points that can then be connected with a rod. As shown in FIG. 2, the screws are placed down the small bony tube created by the pedicle on each side of the vertebra, between the nerve roots. This allows the screws to grab into the bone of the vertebral body, giving them a solid hold on the vertebra. Once the screws are placed, one in each of the two pedicles of each vertebra, they are attached to metal rods that connect the screws together. The screws are placed at two or more consecutive spine segments (e.g., lumbar segment 5 and 6) and connected by the rods.

Generally, a poly-axial pedicle screw assembly, as described in more detail below, includes a tulip-like coupling element that can be coupled to a fixation element, such as, for example, a screw with a head that removably mates with the coupling element. The coupling element and fixation element are configured to be coupled to an elongate stabilizer, such as a rod, that is positioned between a top and a bottom saddle or between a compression member and bottom saddle. A compression member, such as a compression nut, is configured to mate with the coupling element and provides a compressive force to the top and bottom saddles or to the top of the elongate stabilizer rod to secure the elongate stabilizer rod therebetween. The top and bottom saddles are movably positioned within the coupling element such that they can gradually reposition into a secure engagement with the stabilizer as the compression member provides the compressive force.

Figure 3:
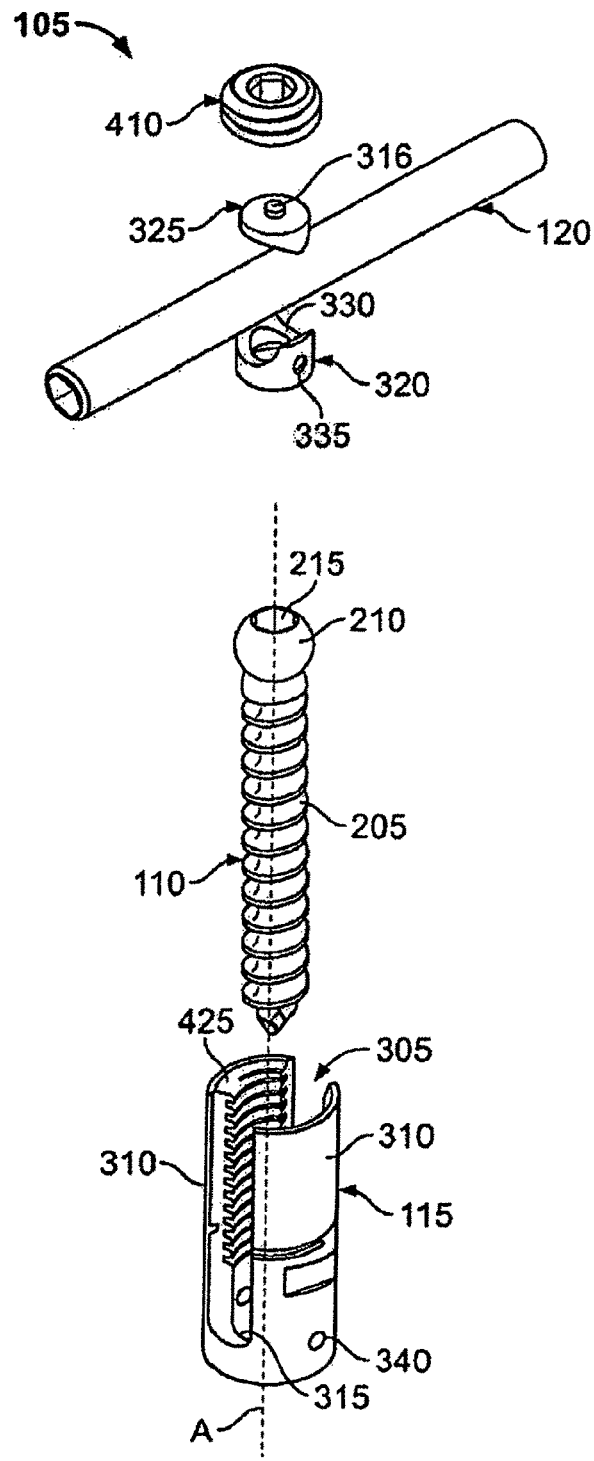
FIG. 3 shows an exploded view of a bone fixation assembly according to one embodiment.

Turning now to FIG. 3, a pedicle screw assembly includes an anchor 105 having a fixation element 110 that is removably coupled to a coupling element 115. The assembly further includes a stabilizer, such as an elongate rod 120, that can be compressively secured to the anchor 105, as described below. As described in detail below, the fixation element 110 can be coupled to a skeletal structure, such as a spinal vertebra by being drilled or screwed into, e.g., a pedicle of a vertebra. The coupling element 115 is used to couple the fixation element 110 to the stabilizer, which can be coupled to multiple fixation elements using additional coupling elements 115.

The fixation element or pedicle screw 110 can include, for example, an elongate screw having a threaded shank portion 205 with external threads that can be screwed into the bone structure, e.g., pedicle, of a vertebra. A head 210 is positioned at the upper end of the shank portion 205. The head 210 has a shape, such as a rounded shape, that is configured to mate with a correspondingly-shaped seat structure in the coupling element 115, as described below. A drive coupler, such as a drive cavity 215 is located within or on the head 210 of the fixation element 110. The drive cavity 215 has a shape that is configured to receive a device that can impart rotational movement to the fixation element 110 in order to screw the fixation element 110 into a bone structure. For example, the drive cavity 215 can have a hexagonal shape that is configured to receive therein an allen-style wrench.

It should be appreciated that the drive coupler need not be a cavity that mates with an allen-style wrench and that other types of drive couplers can be used. Moreover, the fixation element 110 can be in forms other than a shank, including, for example, a hook or clamp. Indeed, it should be appreciated that any structure or component configured for attachment to a bone structure can be used in place of the shank portion of the fixation element.

Figure 4:
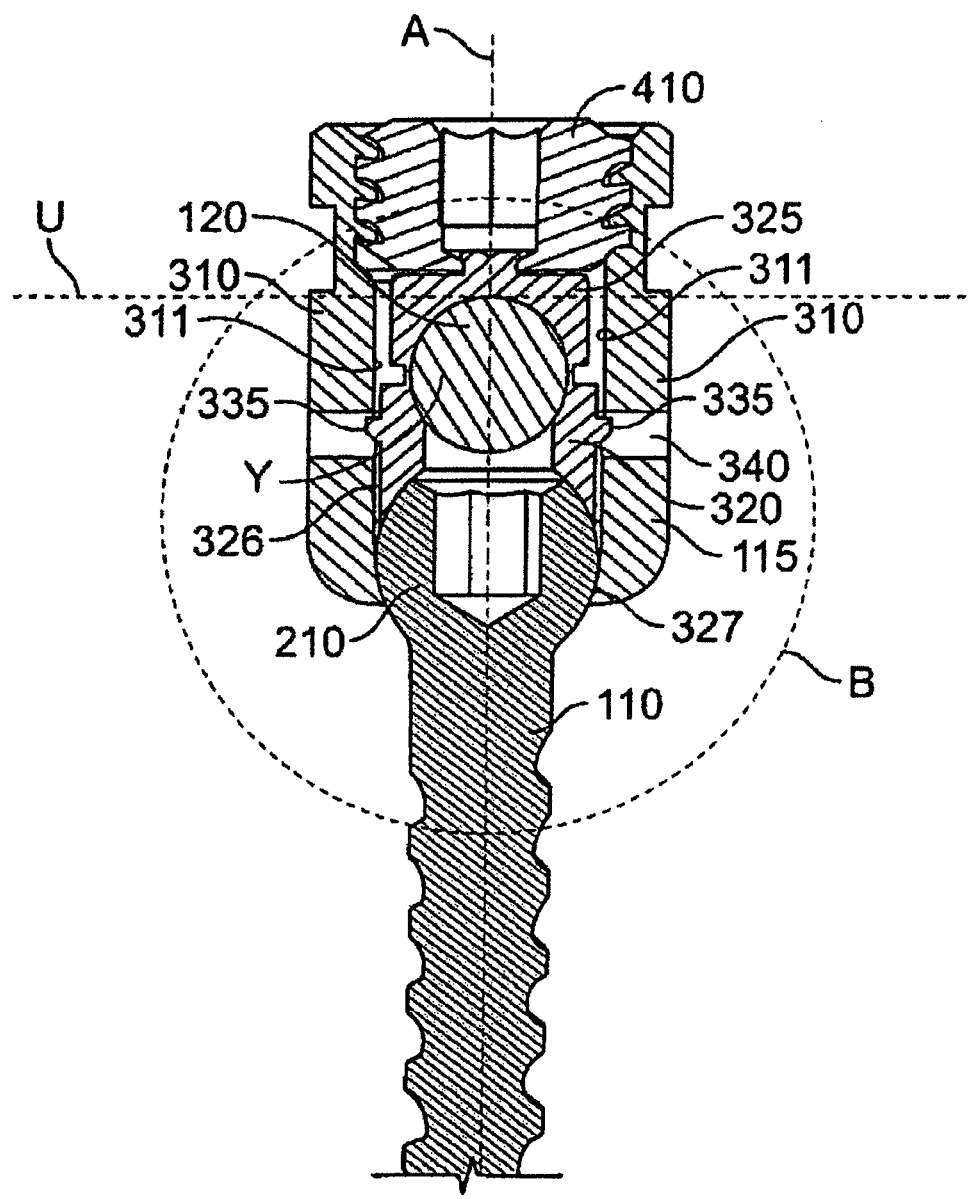
FIG. 4 shows a cross-sectional view of the bone fixation assembly depicted in FIG. 3.

The coupling element 115 is configured to receive the fixation element 110 and the elongate rod 120. The coupling element 115 has an internal bore 305 that extends through the coupling element 115 along an axis A (the axis A is shown in FIGS. 3 and 4). The internal bore 305 is sized to receive at least the shank portion 205 of the fixation element therethrough. A pair of laterally-opposed, upwardly extending projections 310 is separated by the bore 305. The projections 310 have internal, threaded surfaces. In addition, a pair of U-shaped channels 315 extends through the coupling element for receiving therein the rod 120, which extends along an axis that is transverse to the axis A of the bore 305.

The upper ends of the projections 310 define an entry port that is sized to receive therein a compression nut 410, as described below. The compression nut 410 is described herein as having outer threads that are configured to mate with the inner threads on the opposed inner surfaces of the projections 310 of the coupling element 115. As described below, the entry port is sized and shaped to facilitate an easy entry of the compression nut 410 into or over the projections 310 of the coupling element.

A bottom saddle 320 and a top saddle 325 are configured to be positioned within the coupling element 115. The saddles each define a contact surface 330 (shown in FIG. 3) that has a contour selected to complement a contour of the outer surface of the rod 120. In one embodiment, the contact surfaces 330 have rounded contours that complement the rounded, outer surface of the rod 120. However, the contact surfaces 330 can have any shape or contour that complement the shape and contour of the rod 120. The contact surfaces 330 can also be roughed, serrated, ribbed, or otherwise finished to improve the frictional engagement between the saddles 320,325 and the rod. The rod 120 can also be correspondingly roughed, serrated, ribbed, or otherwise finished to further improve the frictional engagement between saddles 320, 325 and the rod.

The complementing shapes and contours between the contact surfaces 330 and rod 120 provide a maximum amount of contact area between the saddles 320, 325 and rod 120. For example, the rod 120 is shown having a rounded or convex outer surface. The contact surfaces 330 of the saddles 320, 325 are correspondingly rounded or concave such that the elongate rod 120 can fit snug between the saddles 320, 325 with the contact surfaces 330 of the saddles 320, 325 providing a wide area of contact with the outer surface of the elongate rod 120. It should be appreciated that the contour and shape of the contact surfaces 330 can be varied to match any contour of the outer surface of the elongate rod 120 or in any manner to maximize the amount of grip between the saddles and the elongate rod.

During assembly of the device, the shank portion 205 of the fixation element 110 is inserted through the bore 305 in the coupling element 115. The rounded head 210 abuts against and sits within a correspondingly-shaped seat 327 in the bottom of the coupling element 115 in a ball/socket manner, as shown in the cross-sectional view of FIG. 4. The seat 327 can have a rounded shape that is configured to provide a secure fit between the head 210 and the coupling element 115. Because the seat 327 is rounded, the head 210 can be rotated within the seat 327 to move the axis of the shank portion 205 to a desired orientation relative to the coupling element 115 and thereby provide a poly-axial configuration.

With the fixation element 110 seated in the coupling element 115, an operator can position the assembly relative to a bone structure such as a vertebra. When the device is fully assembled, the operator can couple a drive device (such as an Allen wrench) to the drive cavity 215 in the head 210 and rotate the fixation element 110 to drive the shank portion 205 into a vertebra or other bone structure. As mentioned, the bottom saddle 320 has an internal bore that is sized to receive therethrough the drive device to provide access to the head 210 of the fixation element 110.

The rod 120 is loaded into the coupling element 115 by inserting the rod downwardly between the projections 310 through the u-shaped channels 315, as shown in FIG. 3. As the rod 120 is moved downwardly into the coupling element 115, the outer surface of the rod 120 will eventually abut and sit against the corresponding rounded contact surface 330 of the bottom saddle 320. The compression nut 410 and attached upper saddle 325 are then threaded downward into the coupling element 115 by mating the external threads on the compression nut 410 with the internal threads on the projections 310 of the coupling element 115. The compression nut 410 can be threaded downward until the rod 120 is compressed between the top and bottom saddles, with the compression nut 410 providing the compression force.

As mentioned, the coupling element 115 has an entry port for the compression nut 410 that facilitates entry or coupling of the compression nut 410 into the coupling element 115. The entry port is defined by the upper edges of the projections 310. The entry port has a structure that guides the compression nut into a proper engagement with the coupling element 115. For example, one or more large chamfers 425 are located on the upper, inner edge of the projections 310 of the coupling element 115 to provide ease of entry for the compression nut 410 into the coupling element 115. In one embodiment, the chamfers 425 are angled with the angle being in the range of thirty degrees to sixty degrees relative to vertical axis A, although the angle can vary. The chamfers 425 guide the compression nut 410 into proper alignment with the coupling element 115 such that the threads on the compression nut properly engage the threads on the opposed projections 310 without any cross-threading.

The compression nut 410 is then threaded downwardly by repeatedly rotating the compression nut 410 about a 360 degree rotation. As the compression nut 410 lowers into the coupling element, the rounded contact surface 330 of the top saddle 325 abuts the rod 120 and compresses the rod 120 against the rounded contact surface 330 of the bottom saddle 320, as shown in FIG. 4. As mentioned the bottom saddle 320 has a floating arrangement with the coupling element 115 and the top saddle 325 is movable and rotatable relative to the compression nut 410. This permits the saddles to gradually reposition themselves into a secure purchase with the rod 120 as the compression nut 410 moves downward. The contact surfaces 330 of the saddles 320, 325 provide a continuous and maximized area of contact between the saddles 320, 325 and the rod 120 for a secure and tight fit therebetween.

Figure 16:
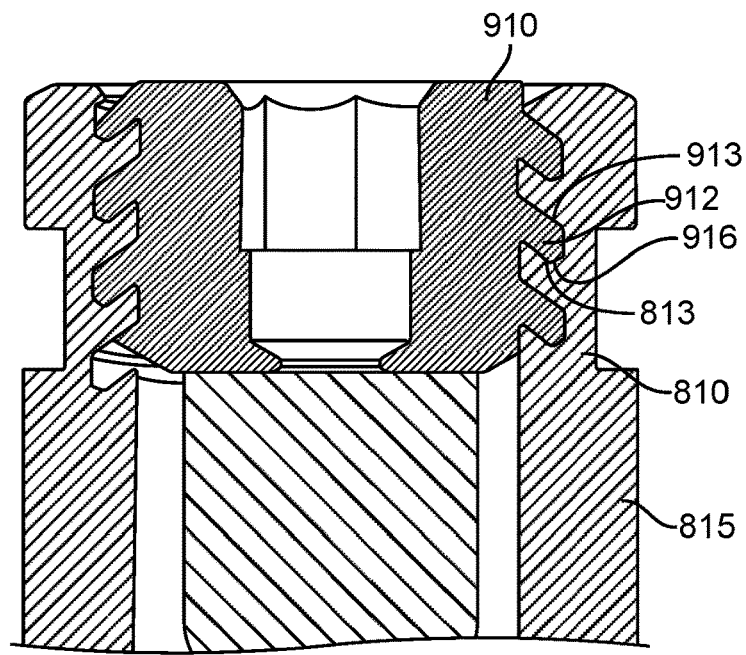
FIG. 16 is a cross-sectional view of a compression element of a bone fixation assembly according to one embodiment.

Moreover, the top saddle 325 is shaped so that opposed wings or protrusions 329 are located on opposed sides of the top saddle 325 (see FIGS. 16-17). The opposed protrusions 329 are positioned on either side of the rod 120 so as to automatically guide the saddle 325 into alignment with the rod 120 as the saddle 325 lowers onto the rod. Because the top saddle 325 can freely rotate as the compression nut lowers onto the rod 120, the protrusions 329 will abut opposed sides of the rod 120 as the top saddle 325 is lowered into the coupling element 115. The top saddle 325 thus self-aligns into a secure engagement with the rod 120 as the top saddle 325 is lowered onto the rod 120.

In one embodiment, the protrusions 329 of the top saddle are formed by a concave contour of the top saddle contact surface 330. It should be appreciated that the protrusions 329 need not be formed from curved surfaces, but can also be formed from straight surfaces. Moreover, the protrusions 329 need not be formed from a continuous, elongated surface, but can rather comprise one or more discrete protrusions, such as spikes, that extend downwardly from the top saddle 325.

As the compression nut 410 is threaded downward, the downward force of the compression nut 410 is transferred to the bottom saddle 320 via the top saddle 325 and the rod 120. This causes the bottom saddle 320 to also move downward so as to press downward against the head 210 of the fixation element 110. The head 210 is thereby pressed downward into the seat 327 in a fixed orientation. In this manner, the position of the fixation element 110 relative to the coupling element 115 is fixed. That is, the head 210 of the fixation element 110 is pressed downward into the seat 327 of the coupling element 115 with a force sufficient to lock the position of the head 210 relative to the coupling element 115.

The compression nut 410 can be tightened to provide a sufficient downward force that locks the positions of the saddles 320, 325 relative to the coupling element 115 and the elongate rod 120. The compression nut 410 thereby provides a downward force that locks the relative positions of the elongate rod 120, saddles 320, 325, coupling element 115, and fixation element 110. After this is complete, the upper portion of the opposed projections 310 of the coupling element can be snapped off at a predetermined location along the length of the projections 310.

As discussed, inner threads are located on the opposed inner faces of the projections 310. The threads extend downwardly along the projections 310 to a depth that is sufficient to provide secure engagement between the threads on the projections 310 and the threads on the compression nut 410 when the compression nut 410 is fully tightened. It should be appreciated that the threads do not have to extend to a depth below the upper surface (identified by line U in FIG. 4) of the rod 120 when the rod 120 is positioned in the coupling element 115. In one embodiment, the threads extend to a depth that is above the upper surface (identified by line U) of the rod 120. The top saddle 325 provides a spacing between the rod 120 and the compression nut 410, which permits such thread depth.

Figure 6A:
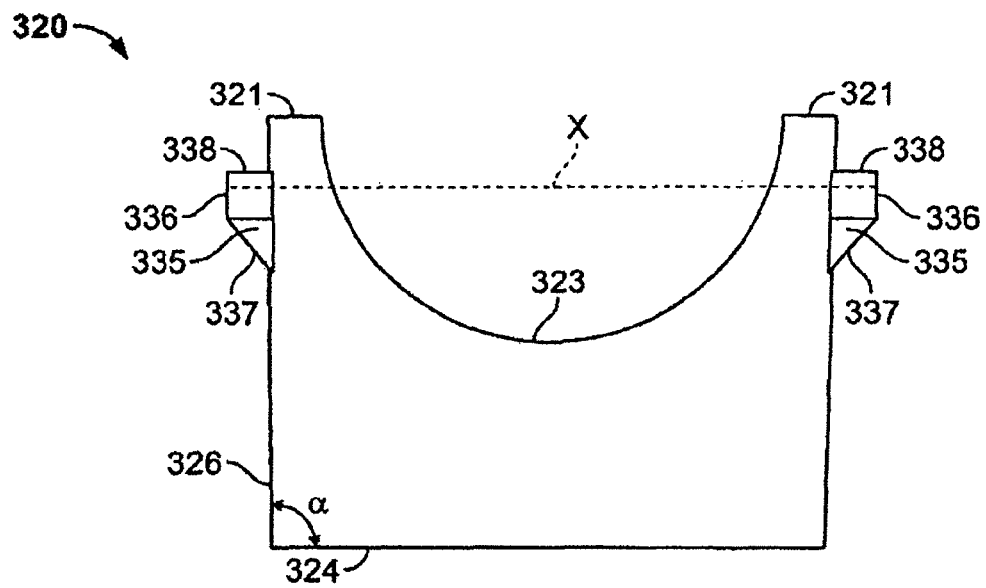
FIG. 6a is a side view of the bottom saddle depicted in FIGS. 3, 4 and 5.
Figure 6B:
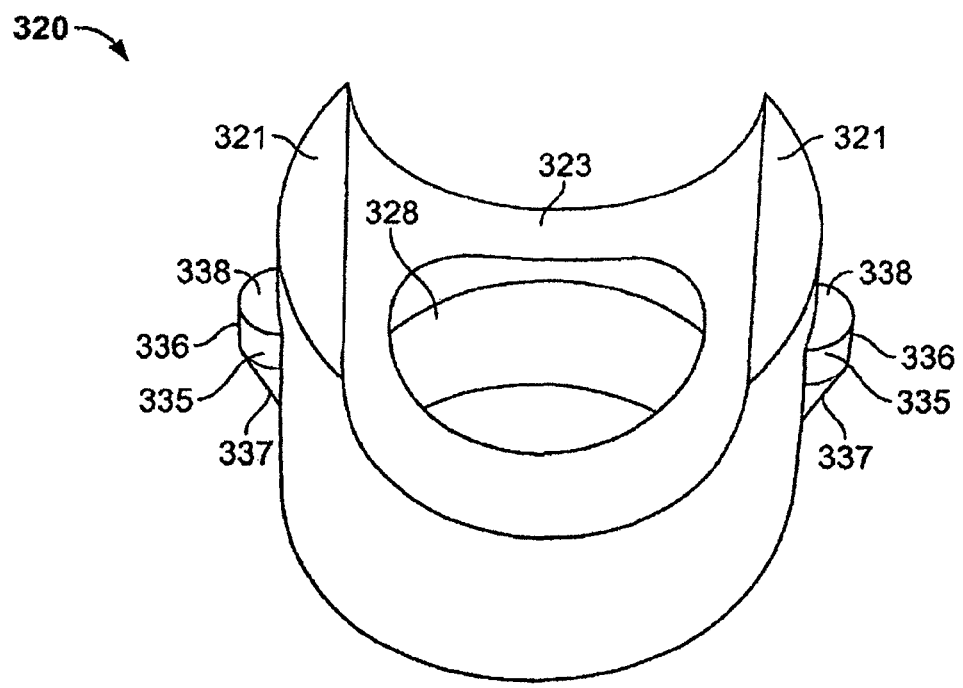
FIG. 6b is a perspective view of the bottom saddle depicted in FIGS. 3, 4 and 5.

As shown in FIGS. 3, 6a and 6b, the bottom saddle 320 has an internal bore 316 that axially aligns with the bore 305 in the coupling element 115 when the bottom saddle 320 is placed in the coupling element 115. The bottom saddle 320 has a cylindrical outer surface 326 forming a pair of opposed walls 321 separated by the internal bore 316 and a rod-receiving region 323. Outer surfaces of the opposed walls 321 include opposing projections 335 that extend laterally from the walls 321. Each of the projections 335 aligns with a corresponding hole or aperture 340 (shown in FIGS. 3 and 4) that extends through the coupling element 115. The opposed walls are generally perpendicular to the base 324 of the saddle 320, as indicated by angle .alpha. shown in FIG. 6A.

As shown in FIG. 4, the bottom saddle 320 is secured within the coupling element 115 by positioning the saddle between the projections 310 such that each projection 335 in the bottom saddle 320 is inserted into a corresponding aperture 340 in the coupling element 115. The bottom saddle 320 is inserted into the coupling element 115 by forcing the saddle 320 down through the projections 310 of the coupling element. The distance X, depicted in FIG. 6a, represents the distance between the outer ends 336 of the projections 335. Distance Y, depicted in FIG. 4, represents the distance between the inner surfaces 311 of the projections 310 of the coupling element 115. Distance X is slightly greater than distance Y. Therefore, saddle 320 must be inserted into the coupling element 115 by forcing it downward through the projections 310 against which the projections 335 will scrape. Once the saddle 320 has been pushed down far enough inside the coupling element 115 that the projections 335 line up with the corresponding apertures 340, the projections 335 will pop into the apertures 340. The projections 335 are shaped to facilitate insertion and retention of the saddle 320 within the coupling element 115. As shown in FIGS. 6a and 6b, the projections 335 have a flat or horizontal proximal surface 338, a rounded side or lateral surface 336, and an angled or ramped distal surface 337. The flat proximal surface 338 prevents the saddle 320 from sliding out of the coupling element 115 in the proximal direction. The angled or ramped distal surface 337 allows the saddle to be guided into the coupling element. The opposed walls 321 can be slightly flexible so that during insertion the walls 321 flex inward toward each other to allow the saddle 320 to be pushed down into the coupling element 115. Once the projections 335 of the saddle 320 reach the apertures 340 of the coupling element, the walls 321 flex back to their natural position and the projections 335 pop into the apertures 340.

The apertures 340 can be round, rectangular, square, oval or any other shape that can receive the projections 335 in a manner that allows the saddle 320 to float in the coupling element 115. Likewise, rather than the shape described above, the projections 335 can be cylindrical, conical, block (rectangular or square), or any other shape that fits within the apertures 340 in a manner that allows the saddle to float in the coupling element 115.

Figure 7:
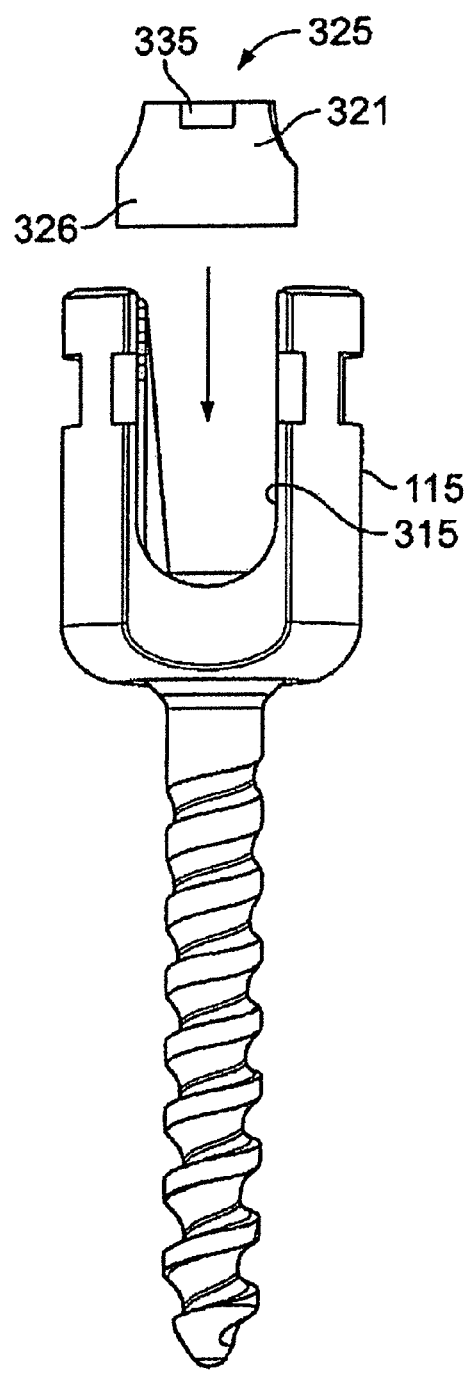
FIG. 7 is a side elevation view of the bottom saddle depicted in FIGS. 6a and 6b as it is loaded into a bone fixation assembly.

Alternatively, the saddle 320 can be inserted into the coupling element 115 in the manner shown in FIG. 7. The saddle 320 is first rotated so that the walls 321 are aligned with the U-shaped channels 315 rather than the projections 310 of the coupling element 115. The diameter of the cylindrical outer surface 326 of the saddle 320 is slightly smaller than the distance Y between the inner surfaces 311 of the projections 310 of the coupling element 115 so that the saddle 320 slides freely into the coupling element 115 without any significant frictional engagement between the saddle 320 and coupling element 115. Once the projections 335 are at the same level as the apertures 340, the saddle 320 is rotated about 90° until the projections 335 pop into the apertures 340. As the saddle is rotated, the projections 335 will scrape against the inner surfaces 311 of the projections 310. The rounded lateral surface 336 of the projections 335 facilitate the rotation of the saddle 320.

As best seen in FIG. 4, the diameter of the aperture 340 can be greater than the distance between the proximal end 338 of the projection 335 and the distal end 337 of the projection 335 by between about 1.0 mm and about 3 mm. In one embodiment, the diameter of the aperture 340 is about 1.0 mm greater than the distance between the proximal end 338 of the projection 335 and the distal end 337 of the projection 335, allowing about 1.0 mm of play between the bottom saddle 320 and the coupling element 115. The diameter of the cylindrical outer surface 326 of the bottom saddle is also less than distance Y between the projections 310. These dimensions permit the bottom saddle 320 to "float" in the coupling element 115 such that the position and the orientation of the bottom saddle 320 can be varied slightly. That is, the bottom saddle 320 can be moved slightly upward or downward and from side to side when mounted in the coupling element 115. The bottom saddle 320 can also rotate slightly when mounted in the coupling element 115. Thus, the bottom saddle 320 can movingly adjust into a secure engagement with the elongate rod 120 when compressed against the elongate rod 120 during assembly, as described below. It can also movingly adjust into a secure engagement with the head portion 210 of the fixation element 110 when pushed down against the head portion 210 by the elongate rod 120.

Figures 5A, 5B:
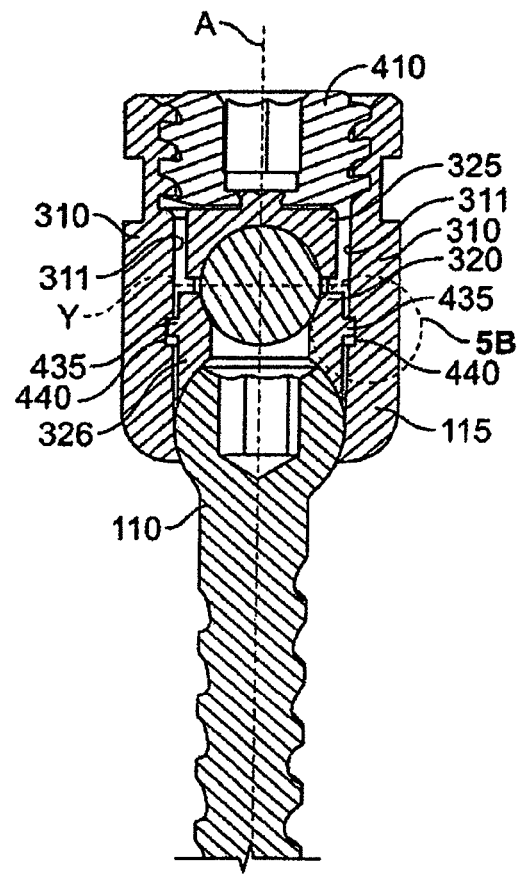

In another embodiment, as shown in FIGS. 5a and 5b, the coupling element 115 has a channel 440 rather than apertures 340. Each of the projections 310 of the coupling element 115 has a channel 440 bored into it, and the channels 440 are aligned with one another and face one another as shown in FIG. 5a. The projections 435 of the saddle 320 can be mated with the channels 440 so as to retain the bottom saddle 320 within the coupling element 115. The saddle 320 shown in FIGS. 5a and 5b can have the same projections 335 as shown in FIGS. 6a and 6b, or it can have square or rectangular block projections 435 as shown in FIGS. 5a and 5b.

As shown in closer detail in FIG. 5b, the lateral ends 436 of the saddle 320 do not make contact with the lateral surface 441 of the channel 440. In other words the distance between the lateral surfaces 441 of the two projections 310 is greater than the distance between the lateral ends 436 of the projections 435 of the bottom saddle 320. Thus, there is no axial force or frictional engagement between the projections 435 and the channels 440. This permits some play between the bottom saddle 320 and the coupling element 115. In addition, the height of the projections 435 (i.e., the distance between the proximal surface 438 and distal surface 437 of the projections 435) is between about 1.0 mm and 3.0 mm less than the height of the channels 440 (i.e., the distance between the proximal inner surface 448 and distal inner surface 447 of the channels 440). In one embodiment, the height of the channels 440 is about 1.0 mm greater than the height of the projections 435, allowing about 1.0 mm of play between the bottom saddle 320 and the coupling element 115. The diameter of the cylindrical outer surface 326 of the bottom saddle is also less than distance Y between the projections 310. These dimensions permit the bottom saddle 320 to "float" in the coupling element 115 such that the position and the orientation of the bottom saddle 320 can be varied slightly. That is, the bottom saddle 320 can be moved slightly upward or downward and from side to side when mounted in the coupling element 115. The bottom saddle 320 can also rotate slightly when mounted in the coupling element 115. Thus, the bottom saddle 320 can movingly adjust into a secure engagement with the elongate rod 120 when compressed against the elongate rod 120 during assembly, as described below. It can also movingly adjust into a secure engagement with the head portion 210 of the fixation element 110 when pushed down against the head portion 210 by the elongate rod 120.

The saddle 320 can be inserted into the coupling element 115 in a manner similar to that shown in FIG. 7. The saddle 320 is first rotated so that the walls 321 are aligned with the U-shaped channels 315 rather than the projections 310 of the coupling element 115. The diameter of the cylindrical outer surface 326 of the saddle 320 is slightly smaller than the distance Y between the inner surfaces 311 of the projections 310 of the coupling element 115 so that the saddle 320 slides freely into the coupling element 115 without any significant frictional engagement between the saddle 320 and coupling element 115. Once the projections 435 are at the same level as the channels 440, the saddle 320 is rotated until the projections 435 slide into the channels 440. The channels 440 can extend along the entire circumference or length of the inner surfaces 311 of the projections 435 so that the projections 435 slide into the channels 440 without running into or contacting the projections 435.

FIGS. 8-11 describe another embodiment, which differs from the other embodiments only with respect to the bottom saddle 520 and retention means for the bottom saddle 520 within the coupling element 115. The bottom saddle depicted in FIGS. 8-11 is designed to permit the opposed walls 521 to tilt toward one another in response to compression forces, and to spring back to their original or resting parallel orientation in the absence of compression forces.

As shown in FIGS. 10a-10d, the bottom saddle 520 has an internal bore 516 that axially aligns with the bore 305 in the coupling element 115 when the bottom saddle 520 is placed in the coupling element 115. The bottom saddle 520 has a cylindrical outer surface 526 forming a pair of opposed walls 521 separated by the internal bore 516 and a rod-receiving region 523. Opposed walls 521 are generally perpendicular to the base 524 of the bottom saddle 520, as indicated by angle .alpha. shown in FIG. 10A. Outer surfaces of the opposed walls 521 include opposing projections 535 that extend laterally from the walls 521. Each of the projections 535 aligns with a corresponding cavity 540 (shown in FIG. 11) that is carved into each of the projections 310 of the coupling element 115. The opposed walls 521 of the saddle 520 are connected to one another by a pair of flexible joints 580 that permit the opposing walls 521 to tilt toward one another in response to compression forces, and to spring back to their original or resting parallel orientation in the absence of compression forces. The flexible joints 580 are formed by a pair of keyhole slots 581 carved into the cylindrical portion 526 of the bottom saddle 520. The keyhole slots 581 are opposite each other and are each aligned about 90° away from each of the projections 535. Consequently, the flexible joints 580 are opposite each other and are each aligned about 90° away from each of the projections 535. The keyhole slots 581 and the flexible joints 580 permit the opposed walls 521 to be squeezed toward one another in response to a compressive force and to spring back into a resting parallel orientation in the absence of a compressive force.

Figure 8A:
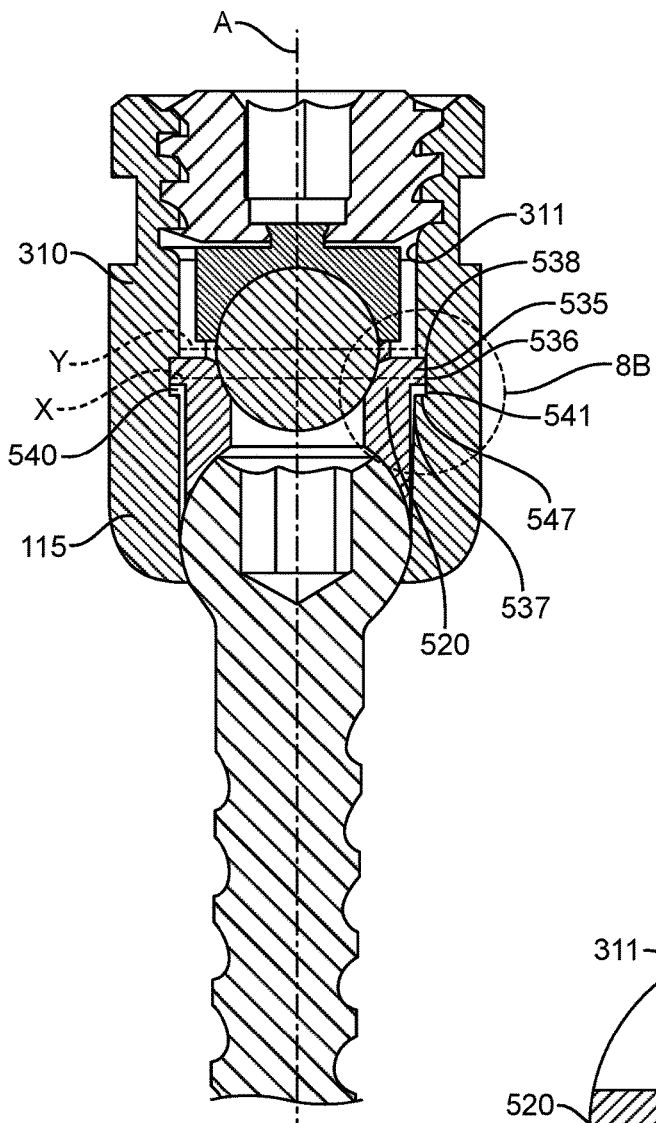
FIG. 8a shows a cross-sectional view of a bone fixation assembly according to another embodiment.
Figure 8B:
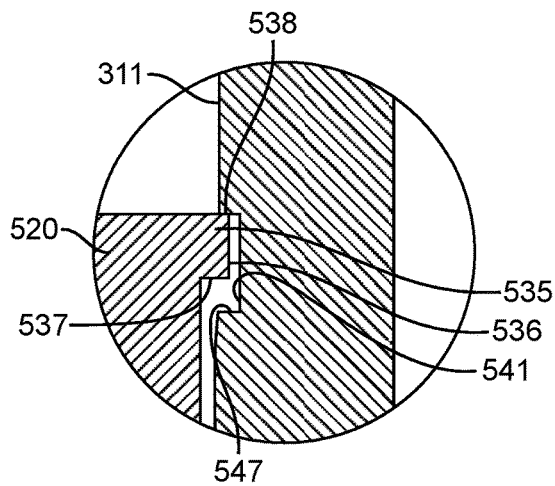
Figure 9:
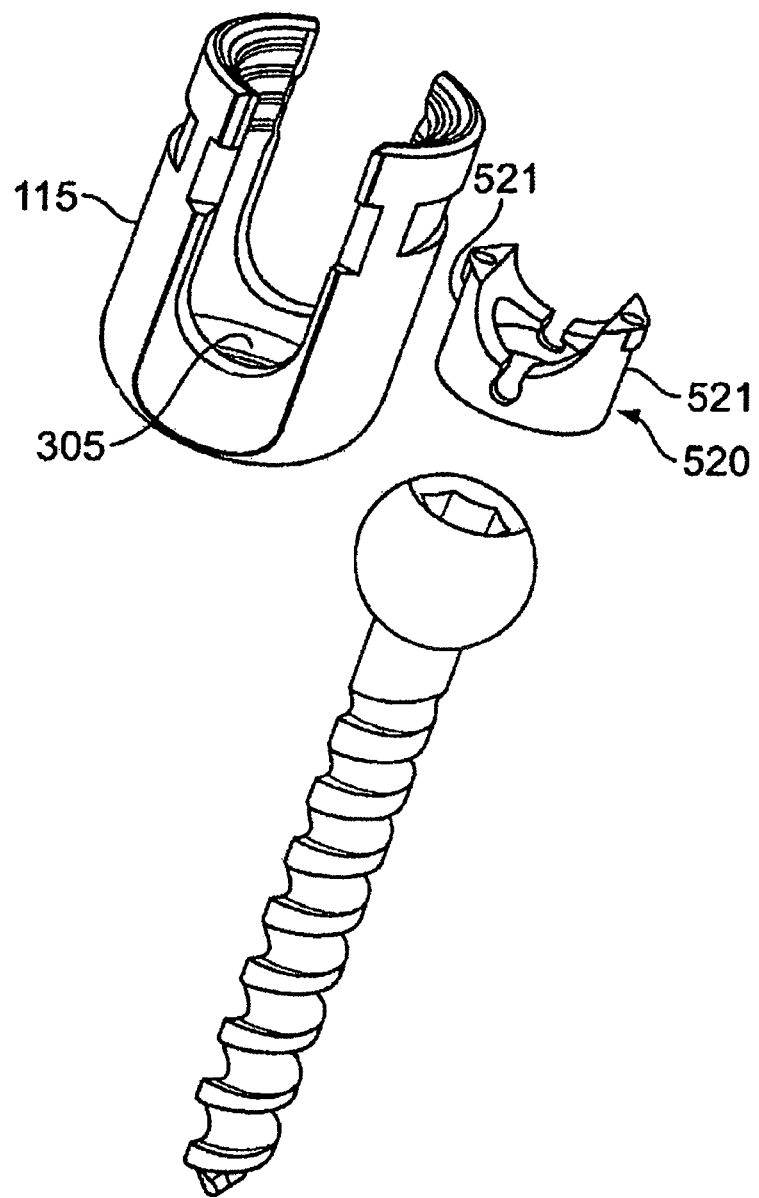
FIG. 9 shows an exploded view of the bone fixation assembly depicted in FIG. 8.
Figure 10A:
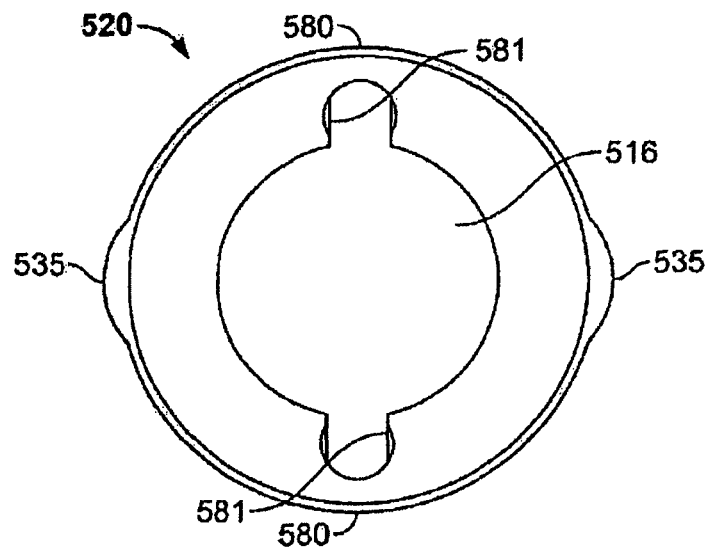
FIGS. 10a-10d show various views of the saddle depicted in the bone fixation assembly depicted in FIGS. 8 and 9.
Figure 10B:
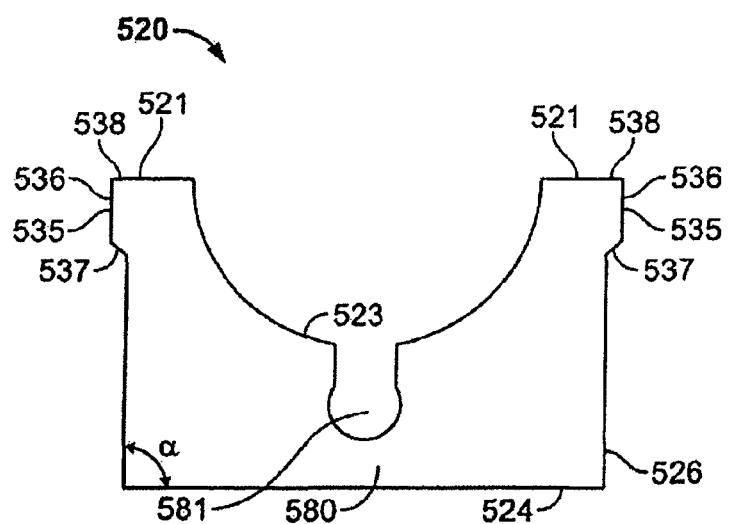
Figure 10C:
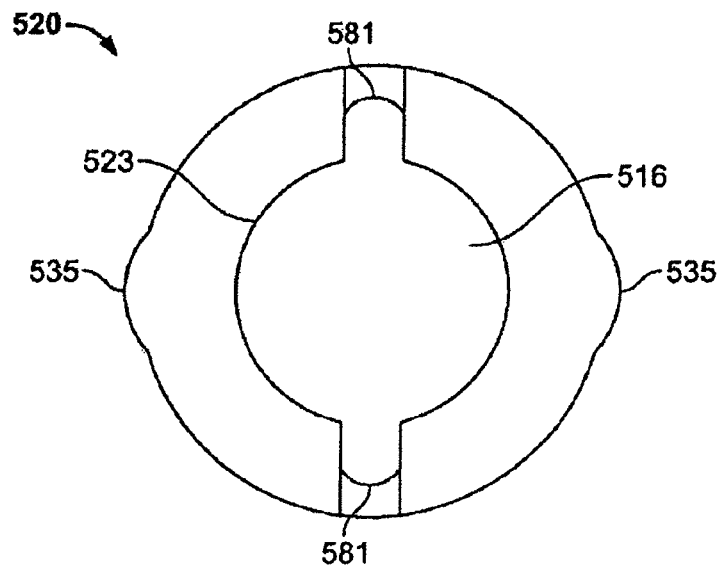
Figure 10D:
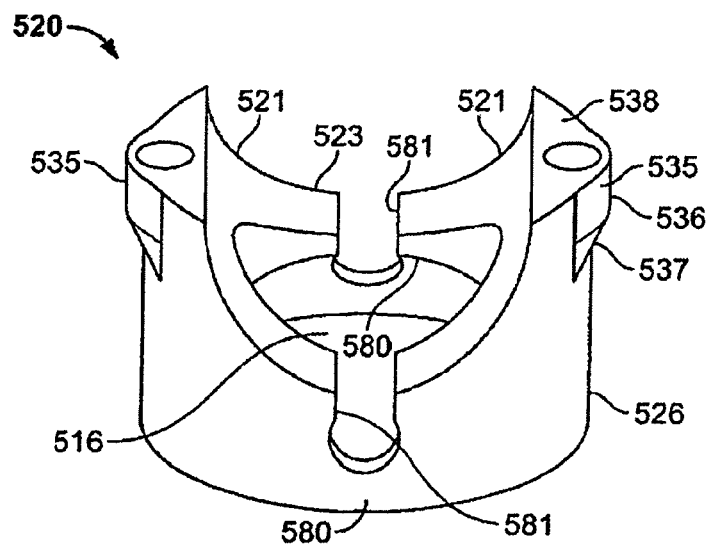
Figure 11:
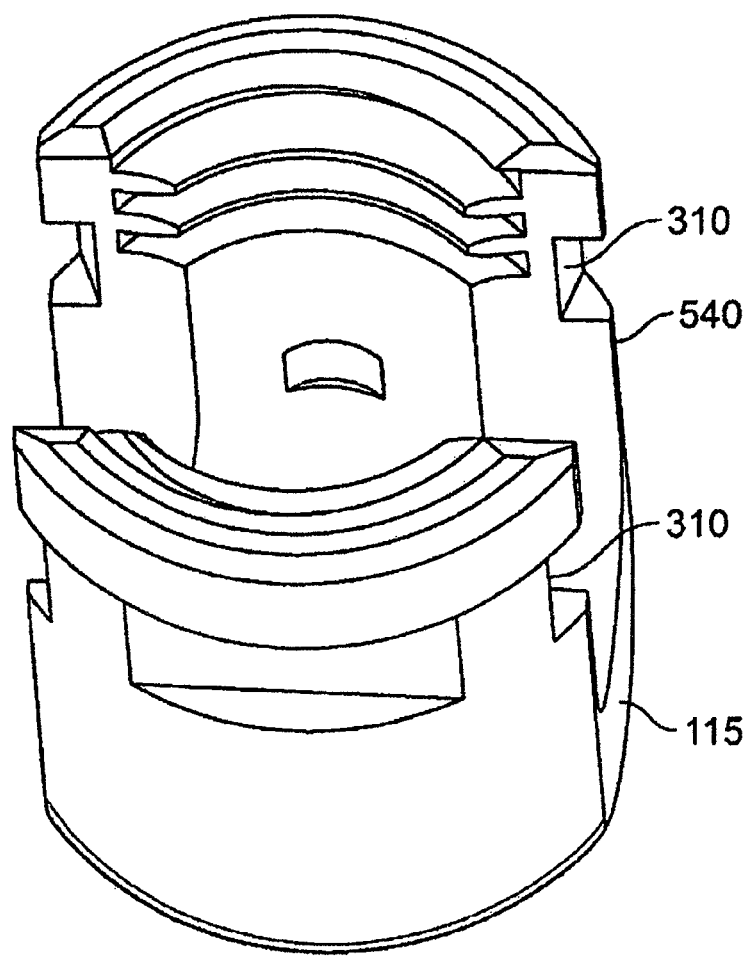
FIG. 11 is a perspective view of the coupling element depicted in the bone fixation assembly depicted in FIGS. 8 and 9.

As shown in FIG. 8, the bottom saddle 520 is secured within the coupling element 115 by positioning the saddle between the projections 310 such that each projection 535 in the bottom saddle 520 is inserted into a corresponding cavity 540 in the coupling element 115. The bottom saddle 520 is inserted into the coupling element 115 by forcing the saddle 520 down through the projections 310 of the coupling element. The distance X, depicted in FIG. 8a, represents the distance between the lateral surface 536 of the projections 535. Distance Y, depicted in FIG. 8a, represents the distance between the inner surfaces 311 of the projections 310 of the coupling element 115. Distance X is slightly greater than distance Y. Therefore, the saddle 520 must be inserted into the coupling element 115 by forcing it downward through the projections 310 against which the projections 535 will scrape. The opposed walls 521 of the saddle 520 can be squeezed toward one another because of the flexible joints 580 and keyhole slots 581 (shown in FIG. 10b). Once the saddle 520 has been pushed down far enough inside the coupling element 115 that the projections 535 line up with the corresponding cavities 540, the projections 535 will pop into the cavities 540. The projections 535 are shaped to facilitate insertion and retention of the saddle 520 within the coupling element 115. As shown in FIGS. 10c and 10d, the projections 535 have a flat or horizontal proximal surface 538, a rounded side or lateral surface 536, and an angled or ramped distal surface 537 (alternatively, the distal surface 537 can be horizontal or flat). The flat proximal surface 538 prevents the saddle 520 from sliding out of the coupling element 115 in the proximal direction. The angled or ramped distal surface 537 allows the saddle to be guided into the coupling element 115. The opposed walls 521 are flexible so that during insertion the walls 521 flex inward toward each other to allow the saddle 520 to be pushed down into the coupling element 115. Once the projections 535 of the saddle 520 reach the cavities 540 of the coupling element 115, the walls 521 flex back to their natural or resting position and the projections 535 pop into the cavities 540.

The cavities 540 can be round, rectangular, square, oval or any other shape that can receive the projections 535 in a manner that allows the saddle 520 to float in the coupling element 115. Likewise, rather than the shape described above, the projections 535 can be cylindrical, conical, block (rectangular or square), or any other shape that fits within the cavities 540 in a manner that allows the saddle 520 to float in the coupling element 115.

Alternatively, the saddle 520 can be inserted into the coupling element 115 in the manner shown in FIG. 7. The saddle 520 is first rotated so that the walls 521 are aligned with the U-shaped channels 315 rather than the projections 310 of the coupling element 115. The diameter of the cylindrical portion 526 of the saddle 520 is slightly smaller than the distance Y between the inner surfaces 311 of the projections 310 of the coupling element 115 so that the saddle 520 slides freely into the coupling element 115 without any significant frictional engagement between the saddle 520 and coupling element 115. Once the projections 535 are at the same level as the cavities 540, the saddle 520 is rotated about 90° until the projections 535 pop into the cavities 540. As the saddle is rotated, the projections 535 will scrape against the inner surfaces 311 of the projections 310. The rounded lateral surface 536 of the projections 535 facilitate the rotation of the saddle 520.

As shown in closer detail in FIG. 5b, the lateral ends 436 of the saddle 320 do not make contact with the lateral surface 441 of the cavities 440. In other words the distance between the lateral surfaces 441 of the two projections 310 is greater than the distance between the lateral ends 436 of the projections 435 of the bottom saddle 320. Thus, there is no axial force or frictional engagement between the projections 435 and the channels 440. This permits some play between the bottom saddle 320 and the coupling element 115. In addition, the height of the projections 435 (i.e., the distance between the proximal surface 438 and distal surface 437 of the projections 435) is between about 1.0 mm and 3.0 mm less than the height of the channels 440 (i.e., the distance between the proximal inner surface 448 and distal inner surface 447 of the channels 440). In one embodiment, the height of the channels 440 is about 1.0 mm greater than the height of the projections 435, allowing about 1.0 mm of play between the bottom saddle 320 and the coupling element 115. The diameter of the cylindrical portion 326 of the bottom saddle is also less than distance Y between the projections 310. These dimensions permit the bottom saddle 320 to "float" in the coupling element 115 such that the position and the orientation of the bottom saddle 320 can be varied slightly. That is, the bottom saddle 320 can be moved slightly upward or downward and from side to side when mounted in the coupling element 115. The bottom saddle 320 can also rotate slightly when mounted in the coupling element 115. Thus, the bottom saddle 320 can movingly adjust into a secure engagement with the elongate rod 120 when compressed against the elongate rod 120 during assembly, as described below. It can also movingly adjust into a secure engagement with the head portion 210 of the fixation element 110 when pushed down against the head portion 210 by the elongate rod 120.

Figure 12A:
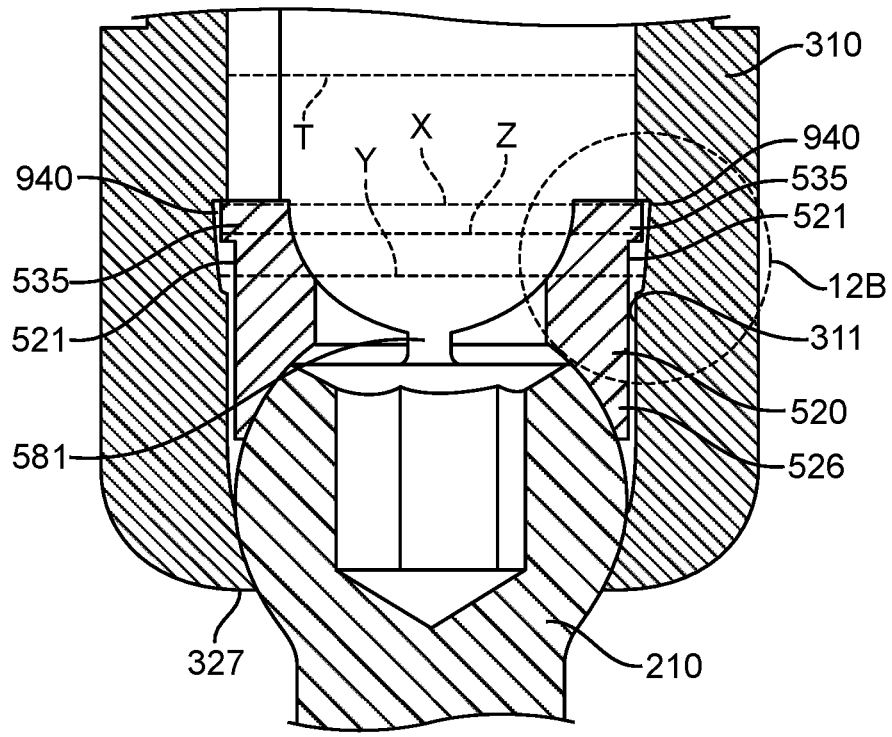
FIG. 12a is a cross-sectional view of a bone fixation assembly according to another embodiment.
Figure 12B:
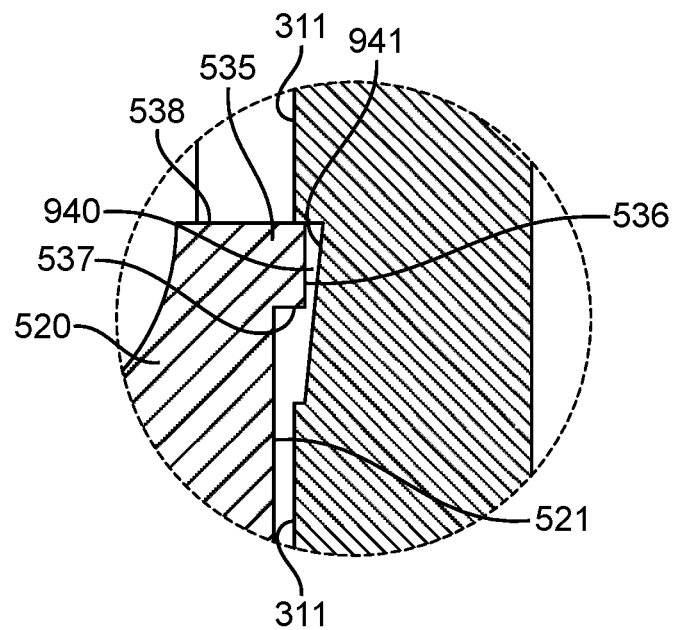

Referring now to FIGS. 12a and 12b, the bottom saddle 520 is the same or substantially the same as bottom saddle 520 shown in FIGS. 8a-10d. The bottom saddle 520 is secured within the coupling element 115 by positioning the saddle between the projections 310 such that each projection 535 in the bottom saddle 520 is inserted into a corresponding cavity 940 in the coupling element 115. The bottom saddle 520 is inserted into the coupling element 115 by forcing the saddle 520 down through the projections 310 of the coupling element. The distance X, depicted in FIG. 12a, represents the distance between the outer ends 436 of the projections 535. Distance T, depicted in FIG. 12a, represents the distance between the inner surfaces 311 of the projections 310 of the coupling element 115. Distance X is slightly greater than distance T. Therefore, saddle 520 must be inserted into the coupling element 115 by forcing it downward through the projections 310 against which the projections 335 will scrape. The opposed walls 521 of the saddle 520 can be squeezed toward one another because of the flexible joints 580 and keyhole slots 581. Once the saddle 520 has been pushed down far enough inside the coupling element 115 that the projections 535 line up with the corresponding cavities or indentations 940, the projections 535 will pop into the cavities 940. The projections 535 are shaped to facilitate insertion and retention of the saddle 520 within the coupling element 115 as described with respect to FIGS. 10c and 10d above. The opposed walls 521 are flexible so that during insertion the walls 521 flex inward toward each other to allow the saddle 520 to be pushed down into the coupling element 115. Once the projections 535 of the saddle 520 reach the cavities or indentations 940 of the coupling element 115, the walls 521 flex back to their natural or resting position and the projections 535 pop into the cavities 940.

The cavities 940 are aligned with one another, but they are not parallel with one another. Instead, as shown in more detail in FIG. 12b and further described below, the cavities 940 are sloped or ramped toward one another in the distal direction.

The cavities 940 each have a proximal region, which is near the top end of the coupling element 115, a middle region distal the proximal region, and a distal region, which is distal the middle region. The distance Z between the proximal regions of the cavities 940 is greater than the distance X between the outer ends 536 of the projections 535, and the distance X is greater than the distance Y between the distal regions of the cavities 940. The proximal region of the cavities 940 each includes a ridge with a drop-off as shown in FIG. 12b. A middle region of the cavities 940, distal the proximal region, forms a ramp that is sloped inward toward a distal direction, wherein the proximal end of the ramp starts at the drop-off and a distal end of the ramp terminates in a distal region that joins the ramp to the inner surface 311 of the wall of the coupling element 115.

In the proximal regions of the cavities, because distance X is less than distance Z, the projections 535 do not make contact with the inner surface 941 of the cavities. Thus, there is no axial force or frictional engagement between the projections 535 and the inner surface 941 of the cavities 940 in the proximal region. This permits some play between the bottom saddle 520 and the coupling element 115 when the bottom saddle is in the proximal region of the cavities 940. In addition, the height of the projections 535 (i.e., the distance between the proximal surface 538 and distal surface 537 of the projections 535) is between about 1.0 mm and 3.0 mm less than the height of the proximal region of the cavities 940. In one embodiment, the height of the proximal region of the cavities 940 is about 1.0 mm greater than the height of the projections 535, allowing about 1.0 mm of play between the bottom saddle 520 and the coupling element 115 when the projections are situated in the proximal region of the cavities 940. The diameter of the cylindrical portion 526 of the bottom saddle is also less than distance Y between the projections 310. These dimensions permit the bottom saddle 520 to "float" in the coupling element 115 such that the position and the orientation of the bottom saddle 520 can be varied slightly while the projections 535 are situated in the proximal region of the cavities 940. That is, the bottom saddle 520 can be moved slightly upward or downward and from side to side when mounted in the coupling element 115 when the projections 535 are situated within the proximal region of the cavities 940. The bottom saddle 520 can also rotate slightly when mounted in the coupling element 115 when the projections 535 are situated within the proximal region of the cavities 940.

As the saddle 520 is forced downward in the distal direction, the distance between the inner surfaces 941, which are in opposite projections 310, becomes smaller because of the sloped ramps. At some point in the middle region of the cavities 940 the projections 535 make contact with the inner surfaces 941 of the cavities 940. As the saddle 520 is further forced in the distal direction, inward axial forces are exerted on the projections 535 and the walls 521 are squeezed into frictional engagement with the sloped ramps. The frictional engagement between the opposing projections 535 and the distal region of the opposing cavities 940 maintains the saddle 520 in frictional engagement with the head portion 210 of the fixation element 110 to prevent relative movement between the fixation element 110 and the coupling element 115 when the stabilizer rod is disengaged from the saddle 520 and the saddle 520 engages the fixation element 110. The fixation element 110 and the coupling element 115 are still manually movable relative to each other in opposition to the frictional engagement when the stabilizer rod is disengaged from the saddle.

FIGS. 13A-14B describe another embodiment, which differs from the previous embodiments only with respect to the bottom saddle 1220 and retention means for the bottom saddle 1220 within the coupling element 115. Like the bottom saddle shown in FIGS. 10A-10D, the bottom saddle 1220 depicted in FIGS. 13A-14B is designed to permit the opposed walls 1221 to tilt toward one another in response to compression forces, and to spring back to their original or resting parallel orientation in the absence of compression forces. The bottom saddle 1220, however, does not have projections that extend laterally from its opposed walls 1221. Instead, the outer surface 1226 of the opposed walls are at an angle .alpha., as shown in detail in FIGS. 14A and 14B. In other words, the walls 1221 are not parallel to one another when the walls 1221 are in a resting or uncompressed state. Instead, they extend away from one another from bottom to top such that the angle .alpha. between the base 1224 of the bottom saddle 1220 and the outer surface of the walls 1226 is an obtuse angle or greater than 90° when the walls 1221 are in a resting or uncompressed state.

As with previous embodiments, the bottom saddle 1220 has an internal bore 1216 that axially aligns with the bore 305 in the coupling element 115 when the bottom saddle 1220 is placed in the coupling element 115. The bottom saddle 1220 has a frustoconical outer surface 1226 forming a pair of opposed walls 1221 separated by the internal bore 1216 and a rod-receiving region 1223. Outer surfaces of the opposed walls 1221 are angled toward one another as explained above. The opposed walls 1221 of the saddle 1220 are connected to one another by a pair of flexible joints 1280 that permit the opposing walls 1221 to tilt toward one another in response to compression forces, and to spring back to their original or resting parallel orientation in the absence of compression forces. The flexible joints 1280 are formed by a pair of keyhole slots 1281 carved into the frustoconical portion 1226 of the bottom saddle 1220. The keyhole slots 1281 are opposite each other. The keyhole slots 1281 and the flexible joints 1280 permit the opposed walls 1221 to be squeezed toward one another in response to a compressive force and to spring back into a parallel orientation in the absence of a compressive force.

Figure 13A:
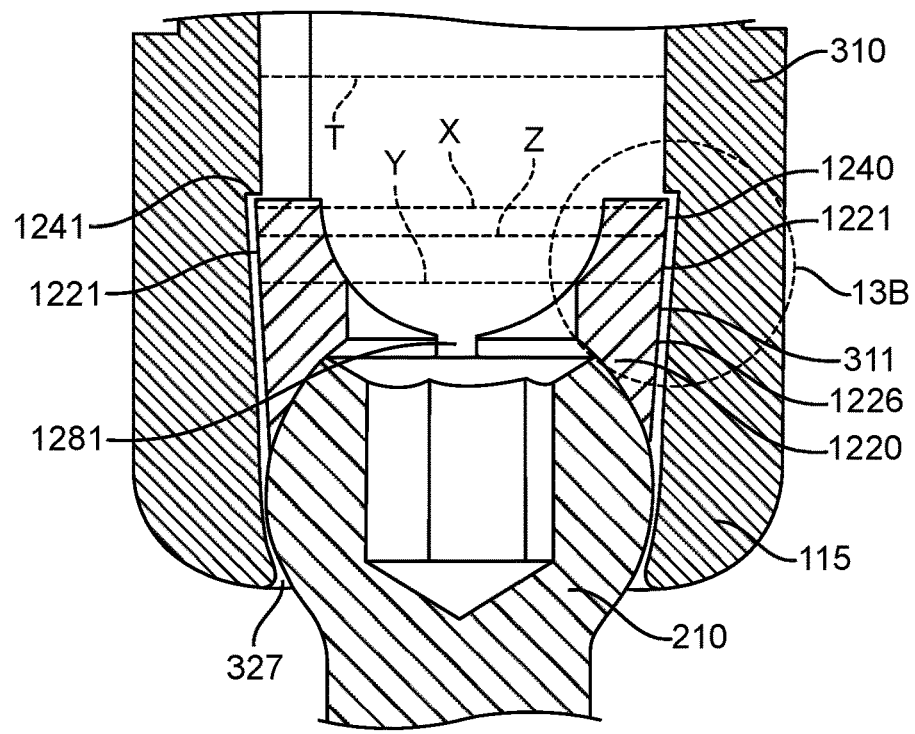
FIG. 13a is a cross-sectional view of a bone fixation assembly according to another embodiment.
Figure 13B:
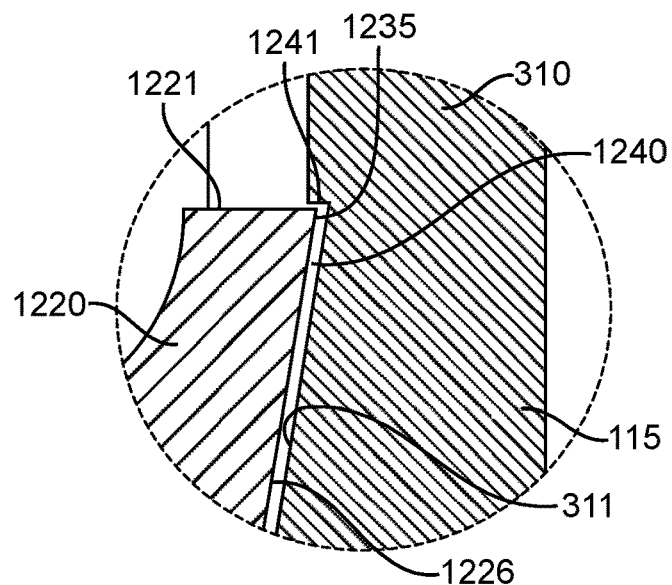
Figure 14A:
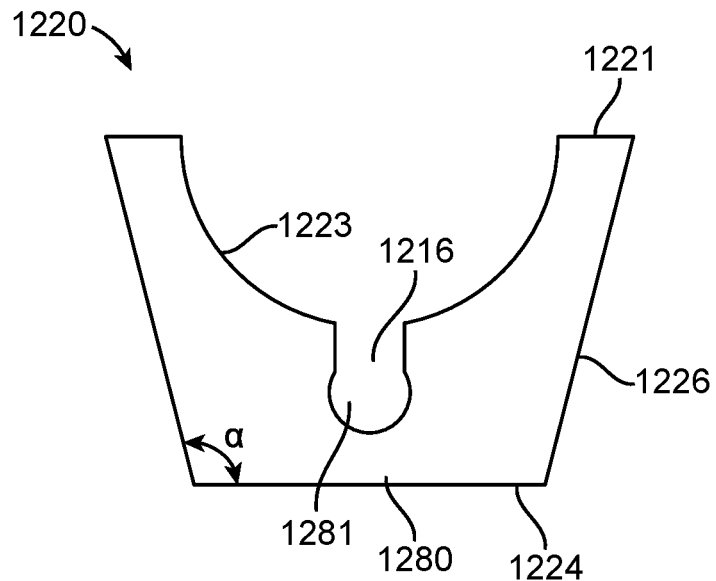
FIG. 14a is a side view of the saddle depicted in the bone fixation assembly depicted in FIGS. 13a and 13b.
Figure 14B:
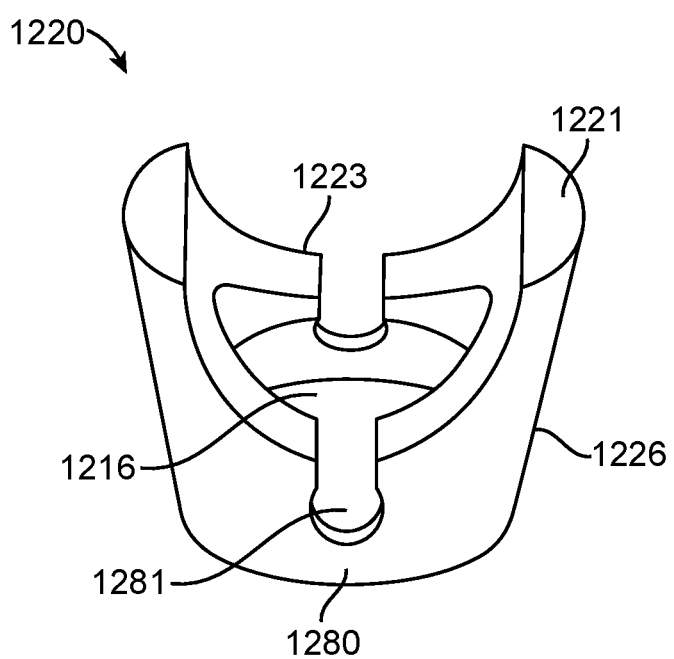

As shown in FIG. 13a, the bottom saddle 1220 is secured within the coupling element 115 by positioning the saddle between the projections 310 such that each of the walls 1221 of the bottom saddle is inserted into a corresponding retention region 1240 in the coupling element 115. The bottom saddle 1220 is inserted into the coupling element 115 by forcing the saddle 1220 down through the projections 310 of the coupling element. The distance X, depicted in FIG. 13a, represents the distance between the outer surface 1226 of walls 1221 in the proximal region 1235 of the walls. Distance T, depicted in FIG. 13a, represents the distance between the inner surfaces of the projections 310 of the coupling element 115 in a region proximal the retention region of the projections 310. The inner surfaces of the projections 310 in a region proximal the retention region form a cylinder, such that the walls are parallel to one another. Distance X is slightly greater than distance T. Therefore, the saddle 1220 must be inserted into the coupling element 115 by forcing it downward through the projections 310 against which the proximal region 1235 of the walls 1221 will scrape. The opposed walls 1221 of the saddle 1220 can be squeezed toward one another because of the flexible joints 1280 and keyhole slots 1281.

The retention region 1240 of the coupling element 115 begins at a proximal ridge 1241 that forms a pop-out with inner surfaces 311. The inner surfaces 311 are not parallel to one another. Instead, they are angled toward one another from a proximal to a distal direction. The inner surfaces 311 can be parallel with the opposed walls 1221 of the saddle such that opposed walls 1221 and inner surfaces 311 are at the same angle relative to the base 1224 of the saddle. For example, if the walls 1221 are at an angle of about 100° to the base 1224, then the inner surfaces 311 can also be at an angle of about 100° relative to the base 1224 of the saddle. Alternatively, the inner surfaces 311 can form a greater angle relative to the base 1224 than the opposed walls 1221, so that the opposed walls 1221 are not parallel to the base 1224. For example, if the walls 1221 are at an angle of about 100° to the base 1224, then the inner surfaces 311 can be at an angle of, e.g., 1050 to the base. The retention regions 1240 of the projections 310 each have a proximal region, which is near the top end of the coupling element 115 just distal the ridge 1241, a middle region distal the proximal region, and a distal region, which is distal the middle region. The distance X between the proximal regions of the retention region 1240 is greater than the distance X between the outer proximal region 1235 of the walls 1221. Distance Z decreases in the distal direction, such that distance Y is less than distance X and distance Z. Thus, once the saddle 1220 has been pushed down far enough inside the coupling element 115 that it reaches the retention region 1240, proximal region 1235 of the walls 1221 will pop into the retention region 1240. In other words, once the proximal region 1235 of the walls 1221 of the saddle 1220 reach the retention region 1240 of the coupling element 115, the walls 1221 flex back to their natural or resting position and pop into the proximal region of the retention region 1240 where there is no compressive force against the walls 1221. Alternatively, the saddle 1220 can be inserted into the coupling element 115 in the manner shown in FIG. 7 and described above.

In the proximal regions of the retention regions 1240, because distance X is less than distance Z, the proximal region 1235 of the walls 1221 do not make contact with the inner surface 311 of the proximal regions of the retention regions 1240. Thus, there is no axial force or frictional engagement between the proximal region 1235 and the inner surface 311 of the retention region 1240. This permits some play between the bottom saddle 1220 and the coupling element 115 when the bottom saddle is in the proximal region of the retention region 1240. At about 1.0 mm below the ridge 1241, the distance between the inner surfaces 311, at distance Y, becomes equal to or less than the distance X, and the proximal region 1235 of the walls 1221 makes contact with the inner surface 311 of the retention regions 1240. This allows about 1.0 mm of play between the bottom saddle 1220 and the coupling element 115 when the proximal regions 1235 of the walls' 1221 are situated in the proximal region of the retention region 1240. These dimensions permit the bottom saddle 1220 to "float" in the coupling element 115 such that the position and the orientation of the bottom saddle 1220 can be varied slightly while the proximal regions 1235 s are situated in the proximal region of the retention region 1240. That is, the bottom saddle 1220 can be moved slightly upward or downward and from side to side when mounted in the coupling element 115 when the proximal regions 1235 are situated within the proximal region of the retention region 1240. The bottom saddle 1220 can also rotate slightly when mounted in the coupling element 115 when the proximal regions 1235 are situated within the proximal region of the retention region 1240.

As the saddle 1220 is forced downward in the distal direction, the distance between the inner surfaces 311, which are opposite projections 310, becomes smaller because of the angled or sloped inner surfaces 311. At some point in the middle region of the retention region 1240, as explained above, the proximal regions 1235 make contact with the inner surfaces 311 of the retention region 1240. As the saddle 1220 is further forced in the distal direction, inward axial forces are exerted on the proximal regions 1235 of the walls 1221, and the walls 1221 are squeezed into frictional engagement with the sloped surfaces 311 of the retention region 1240. The frictional engagement between the proximal regions 1235 and the distal region of the retention region 1240 maintains the saddle 1220 in frictional engagement with the head portion 210 of the fixation element 110 to prevent relative movement between the fixation element 110 and the coupling element 115 when the stabilizer rod is disengaged from the saddle 1220 and the saddle 1220 engages the fixation element 110. The fixation element 110 and the coupling element 115 are still manually movable relative to each other in opposition to the frictional engagement when the stabilizer rod is disengaged from the saddle 1220.

Figure 18A:
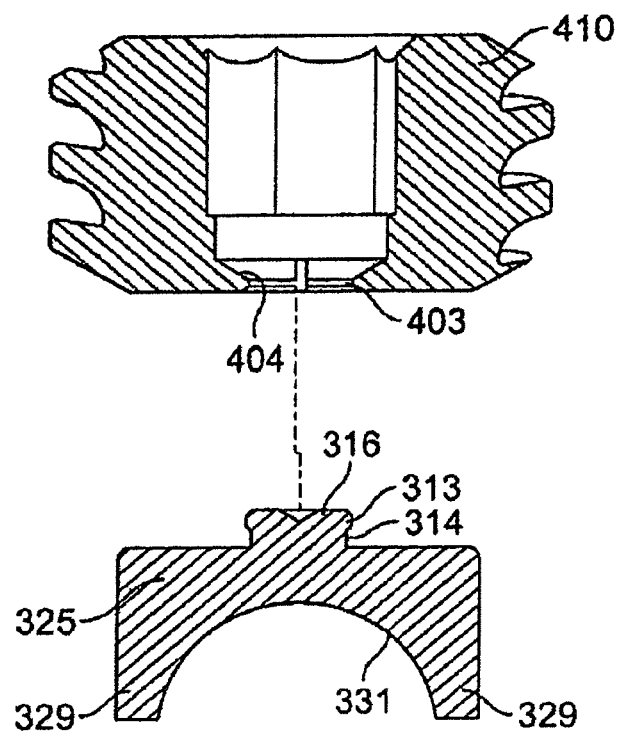
FIG. 18a is a cross-sectional exploded view of a compression nut and top saddle according to one embodiment.
Figure 18B:
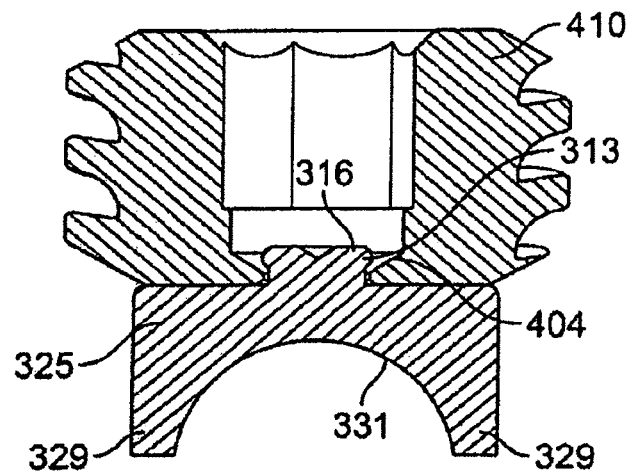

Referring now to FIGS. 18a and 18b, the top saddle 325 is rotatingly mounted within a compression nut 410 that has outer threads that are configured to mate with the threads on the internal surface of the opposed projections 310 of the coupling element 115. In this regard, the top saddle 325 has an upper projection 316 that rotatingly mates with the compression nut 410 and permits the top saddle 325 to rotate and/or tilt relative to the compression nut 410 when attached thereto. The projection 316 has a lip portion 313 and a neck portion 314 connecting the lip portion to the saddle 325. The lip portion 313 of the projection 316 can be snapped into an opening 403 in the bottom of the compression nut 410. Once snapped in, the lip portion 313 rests against an angled ledge 404 formed in a bore just above the opening 403 of the compression nut 410. When attached, the top saddle 325 is positioned immediately below the compression nut 410 and can rotate relative to the compression nut 410.

Figure 19A:
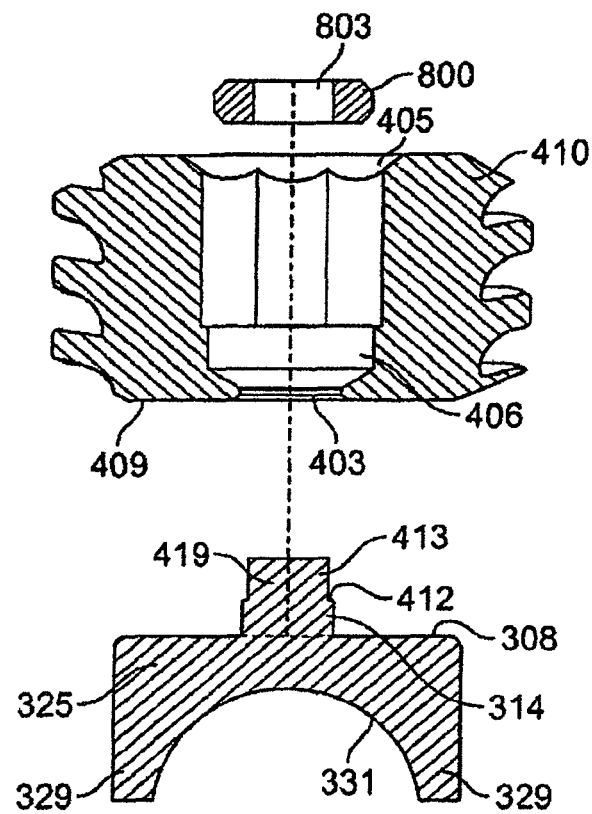
FIG. 19a is a cross-sectional exploded view of a compression nut and top saddle according to another embodiment.
Figure 19B:
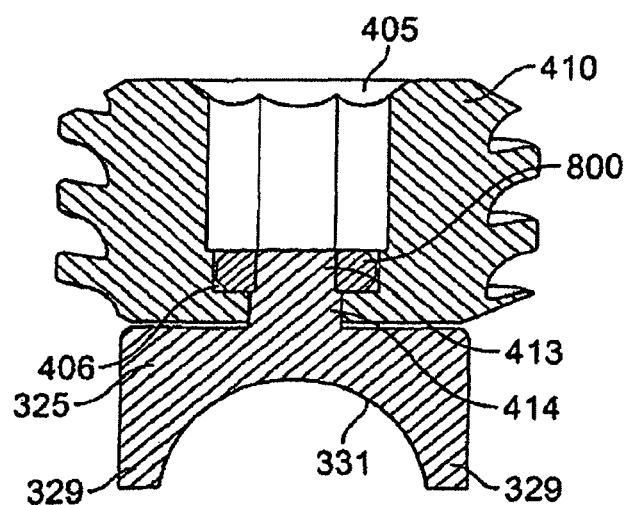

In another embodiment shown in FIGS. 19a and 19b the top saddle 325 has a projection 316 with a neck portion 314 and an lip portion 313. The circumference of the neck portion 314 is greater than the circumference of the lip portion 313 and a step 312 is formed therebetween. The neck portion 314 and lip portion 313 are inserted through an opening 403 in the bottom of the compression nut 410 that leads to a chamber 406 for receiving a friction nut 800. The friction nut 800 is inserted through a top opening 405 in the compression nut 410. The friction nut 800 has a center bore 803 with a circumference that is slightly smaller than the circumference of the lip portion 313 of the projection 316 and significantly smaller than the circumference of the neck portion 314. The outer circumference of the friction nut 800 is slightly smaller than the circumference of the chamber 406. The portion of the engagement portion 314 that is inserted into the chamber 406 is threaded through the central bore 803 of the friction nut 800. The neck portion 314 and central bore 803 are forced into tight frictional engagement with one another so that they cannot be disengaged without significant forces acting on them. The bottom end of the friction nut abuts the step 312. The circumference of the friction nut 800 allows it to rotate within the chamber 406. The circumference of the neck portion 314 is dimensioned so that it can rotate within the opening 403. The neck portion 314 is long enough so that there is a small gap between the top surface 308 of the top saddle 325 and the bottom surface 409 of the compression nut 410. These dimensions permit the bottom saddle 325 to rotate relative to the compression nut 410.

In another embodiment, the top saddle 325 is fixedly attached to the compression nut 410 such that it does not rotate relative to the compression nut. In another embodiment, there is no top saddle and the compression nut directly contacts the stabilizer rod.

When the compression nut 410 is attached to the top saddle 325, the compression nut 410 is rotatingly coupled to the coupling element 115 by mating the outer threads of the compression nut 410 with the inner threads of the coupling element 115. The compression nut 410 is repeatedly rotated over a 360 degree rotational angle to lower the compression nut into the coupling element. The compression nut 410 is described herein as having outer threads that mate with inner threads on the opposed projections 310. As described below, this advantageously permits a thread configuration that prevents projections 310 from spreading apart from one another as the compression nut 410 is screwed into the coupling element 115. However, it should be appreciated that the compression nut 410 can be modified to have an annular shape with internal threads that mate with corresponding outer threads on the opposed projections 310.

As best shown in FIG. 4, the threads on the inner surfaces of the projections 310 of the coupling element 115 are tilted inwardly with respect to a horizontal axis (a horizontal axis is perpendicular to the axis A shown in FIGS. 3 and 4). The threads on the exterior of the compression nut 410 are correspondingly tilted. The tilted thread configuration causes the compression nut 410, when screwed into the coupling element 115, to prevent the projections 310 from spreading apart relative to one another. Rather, the compression nut 410 applies a radially inward (i.e., toward the axis A) force to the projections 310 as the compression nut 410 is screwed into the coupling element 115. This keeps the projections 410 from spreading apart while the compression nut 410 is screwed into the coupling element 115.

In addition, the threads are buttressed such that it requires less force to lower or tighten the compression nut 410 into the coupling element 115 and greater force to untighten or loosen the compression nut 410 relative to the coupling element 115. In this manner, it is unlikely that the compression nut will inadvertently loosen from the coupling element over time. This is advantageous, as the assembly can often be mounted in a vertebra for an extended period of time (such as several years) and it is undesirable for the compression nut to inadvertently loosen from the coupling element.

Other advantageous embodiments of the compression nut are shown in FIGS. 15A-17C. Bone fixation system shown in FIGS. 15A-15C shows a compression nut 710 with an external thread 712 that has both a load flank 713 and a stab flank 714 that are tilted inwardly in a downward direction toward the distal or bottom end 718 of the compression nut 710 and away from the proximal or top end 717 of the compression nut 710. Thread 712 has a load flank 713 that is sloped such that for a given cross-section of the thread through a longitudinal axis A of compression nut 710, a point on load flank 713 at a root 711 of thread 710 is closer to the top end 717 of compression nut 710 than a point on load flank 713 at a crest 716 of thread 712.

To define the angles of the thread surfaces, plane B normal to longitudinal axis A is also shown. Angle .alpha. represents the angle measured clockwise from thread root 711 at plane B to stab flank surface 714. Load flank 713 is at a downward curved slope from thread root 711 to thread crest 716. Stated somewhat differently, load flank 713 forms a concave shape from thread root 711 the thread crest 716 in which thread root 711 is closer to top end 717 of compression nut 710 than is thread crest 716.

Coupling element 615 has an internal thread 612 that complements and mates with external thread 712 of compression nut 710. When measured clockwise from normal plane B to clearance flank surface 614, clearance flank 614 of internal thread 612 forms an angle that is of substantially the same magnitude as angle .alpha. Stab flank 613 forms a convex shape from thread root 611 to thread crest 616. Thus, thread 712 of compression nut 710 and thread 612 of coupling element 615 are engaged when compression nut 710 is threadedly engaged within internal bore 605 of coupling element 615. Angle .alpha. can be between about −1° and about −40°. In accordance with various embodiments, angle .alpha. can be about −1°, about −5°, about −10°, about −15°, about −20°, about −25°, about −30°, about −35°, or about −40°.

The thread configuration shown in FIGS. 15A-15C causes the compression nut 710, when screwed into the coupling element 615, to prevent the projections 610 from spreading apart relative to one another. Rather, the compression nut 710 applies a radially inward (i.e., toward the axis A) force to the projections 610 as the compression nut 710 is screwed into the coupling element 615. This keeps the projections 610 from spreading apart while the compression nut 710 is screwed into the coupling element 615.

More specifically, the way in which the thread geometry of the embodiment shown in FIGS. 15A-15C prevents splaying is based on the formation of a crest/root interference fit. Any outward, splaying force on the arms 610 of the coupling element 615 manifests itself in a force having two components: (1) a lateral component; and (2) an upward component. The upward component of the force causes crest 616 of thread 612 of coupling element 615 to arc up resulting in crest 616 getting lodged into root 711 of thread 712 of compression nut 710. The lateral component causes clearance flank 614 of thread 612 of coupling element 615 to push laterally against stab flank 714 of thread 712 of compression nut 710. Due to the angle of the stab flank 714, this lateral force pulls thread 712 downward into an interference fit between crest 716 and root 611. This dual-interference fit mechanism provides increased anti-splaying properties. Need to describe items 611 and 613 shown in FIGS. 15A-15C.

FIG. 16 shows a compression nut 910 with threads 912 that are tilted inwardly in the same manner as those in FIG. 12. Thread 912 of compression nut 410 is similar to thread 712 of compression nut 710, except that load flank 913 of thread 912 is linear rather than curved or concave and thread crest 916 forms a point. As with the embodiment shown in FIGS. 15A-15C, coupling element 815 has an internal thread 812 that complements and mates with external thread 912 of compression nut 10. Stab flank 813 of thread 812 is also linear rather than curved or convex.

Figure 17A:
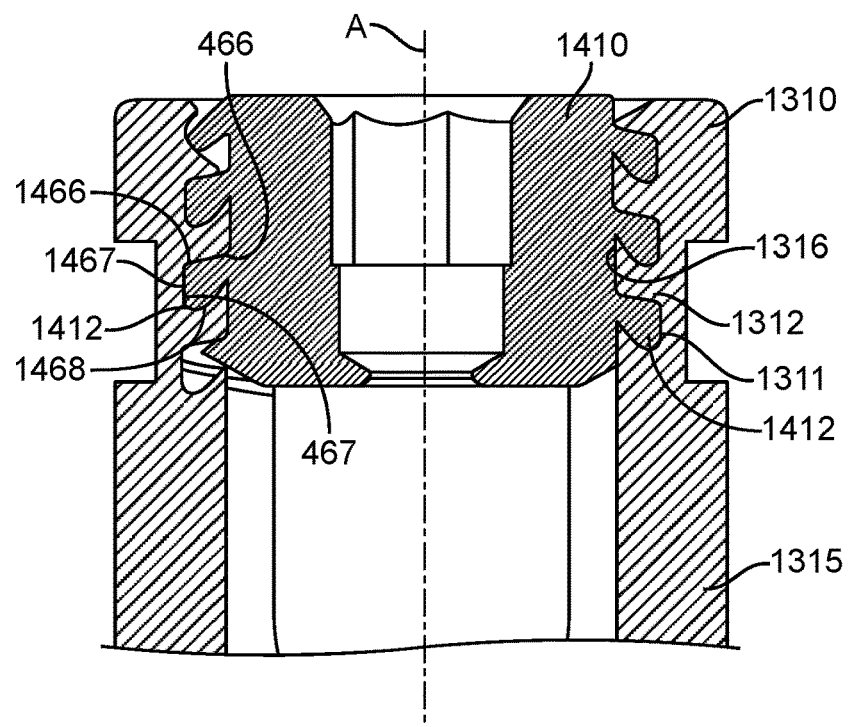
FIG. 17a is a cross-sectional view of a compression element of a bone fixation assembly according to another embodiment.
Figure 17B:
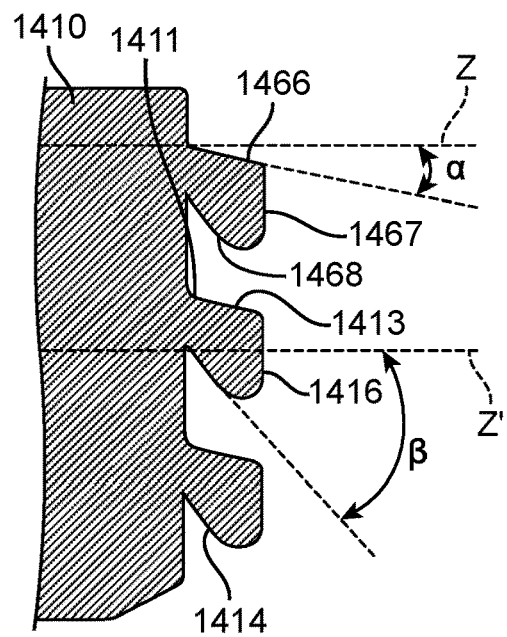
Figure 17C:
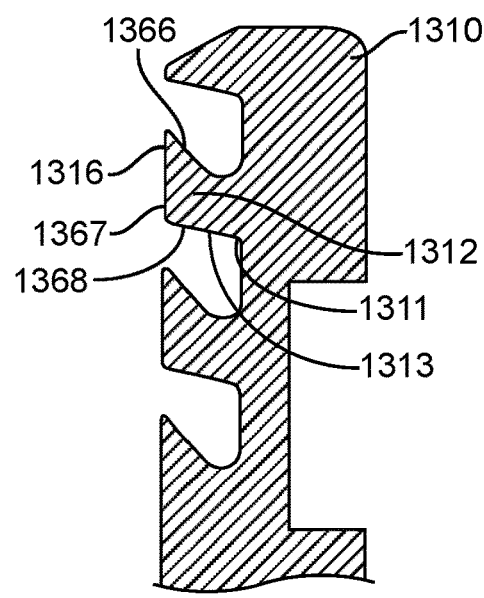

FIGS. 17A-17C show another embodiment of a compression nut 1410 and corresponding coupling element 1315 with threads having a specific geometry. The internal threads 1312 of the coupling element include a forward-facing thread surface or load flank 1313 that is sloped so that, for a given cross-section of the thread 1312 through the longitudinal axis of the coupling element 1315, a point on the load flank surface 1313 at the crest 1316 of the thread 1312 is closer to the proximal or top of the coupling element 1315 than a point on the load flank surface 1313 at the root 1311 of the thread 1312.

External threads 1412 of the compression nut 1410 have a specific geometry that complements the geometry of the threads 1312 of the coupling element 1315. The rearward-facing or proximal facing thread surface (load flank surface 1413) is sloped or angled so that, for a given cross-section of the thread 1412 through the longitudinal axis of the compression nut 1410, a point on the load flank surface 1413 at the root 1411 of the thread 1412 is closer to the proximal end or top of the compression nut 1410 than a point on the load flank surface 1413 at the crest 1416 of the thread 1412, resulting in an angle .alpha. measured clockwise from a normal plane, such as plane Z, to the load flank surface 1413. Angle .alpha. can be between about −1° and about −40°. In accordance with various embodiments, angle .alpha. can be about −1, about −5°, about −10°, about −15°, about −20°, about −25°, about −30°, about −35°, about −37°, or about 40°. The forward-facing or distal facing thread surface (stab flank surface 1414) is sloped or angled at an angle .beta. measured clockwise from normal plane Z', to the stab flank surface 1414. Plane Z' is parallel to plane Z. Angle .beta. can be between about −1° and about −40°. In accordance with various embodiments, angle .beta. can be about −1°, about −5°, about −10°, about −15°, about −20°, about −25°, about −30°, about −35°, about −37°, or about −40°.

The way in which the thread geometry shown in FIGS. 17A-17C prevents splaying is based on the formation of a crest/root interference fit. Any outward, splaying force on the projections 1310 of the coupling element 1315 manifests itself in a force having two components: (1) a lateral component; and (2) an upward component. The upward component of the force causes the crest of the internal thread to arc up resulting in the crest of the internal thread getting lodged into the root of the external thread. The lateral component causes the rearward-facing or clearance flank of the internal thread to push laterally against the forward-facing or clearance flank of the external thread. Due to the angle of the clearance flank, this lateral force pulls the fastener thread downward into an interference fit between the crest of the external thread and the root of the internal thread. This dual-interference fit mechanism improves anti-splaying properties.

The thread geometry shown in FIGS. 17A-17C is also directed to the issue of torque vs. rotational displacement of the compression nut 1410. It can be desirable to stiffen the response of the fastener to torque in order to increase the amount of torque required to unscrew the compression nut. An improved response results from increasing the contact surface area, and consequently the frictional forces, between the internal threads 1312 of the coupling element 1315 and external threads 1412 of the compression nut 1410 in the manner shown in FIGS. 17A-17C. Specifically, thread 1412 has three main sides: a proximal side 1466, a lateral side 1467, and a distal side 1468. These three main sides of thread 1412 make contact with thread 1312, which has a corresponding proximal side 1366, lateral side 1367 and distal side 1368. This results in an increase in contact surface area of approximately 20% over a buttress, v-shaped, or reverse-angle thread having only two main sides.

Post operative loosening of spinal fusion constructs and migration of locking nuts or set screws might occur if insufficient torque is applied during final tightening or if implant components are misaligned during installation. The present disclosure is intended to prevent such construct loosening or locking nut or set screw disengagement by having a series of radii surfaces on the top portion of the set screw, or compression nut, that engage with radii surfaces of the corresponding screw head, or coupling element. The advancement of the compression nut is completely normal until the top portion starts engaging with the coupling element. From that point, at each turn by hand, for example by using a hexalobe driver tool, symmetrical radii protrusions of the compression nut forces the walls of the coupling element to open slightly, to splay, or to deflect away from each other. When radii surfaces of the two engaging parts pass each other, the splayed pedicle screw walls return to the original position to lock or engage corresponding radii surfaces of the engaging parts. Since the locking feature is fully symmetrical, removal of the compression nut is completed with the same ease in the opposite direction.

Figure 20:
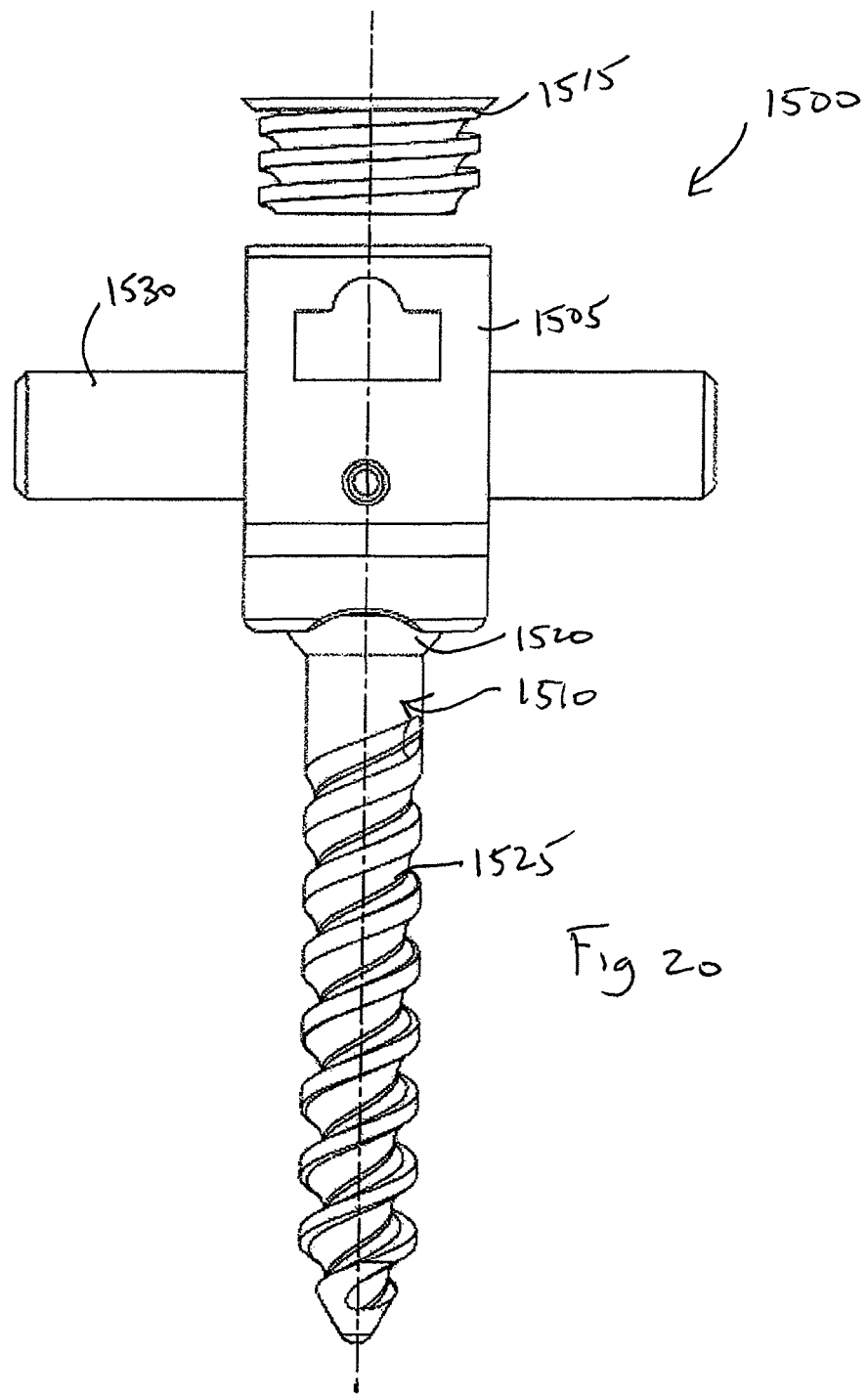
FIG. 20 is a side view of embodiments of an anchor assembly described herein.

With reference to FIG. 20, an anchor 1500 is shown having, a coupling element 1505, a pedicle screw 1510, and a compression nut 1515. The anchor 1500 can incorporate anchor embodiments that are described above, and the anchor 1500 can function in the same manner as described with respect to other anchor embodiments. For example, as described in other embodiments, the pedicle screw 1510 can include a head 1520 and a threaded shank portion 1525. The coupling element 1505, as described in other embodiments, preferably is configured to receive a rod 1530 that extends to other anchors for securing or stabilizing vertebrae. The compression nut 1515 is threadingly rotated into the coupling element 1505.

FIGS. 21A and 21B depict cross-sectional and partially exploded views of the anchor 1500 shown in FIG. 20. The coupling element 1505 preferably includes an internal bore 1535 that is configured to receive at least a portion of the pedicle screw 1510. The internal bore 1535 also includes laterally opposed upwardly extending projections 1540. The upwardly extending projections 1540 preferably include internal threads 1545 that are configured to receive the compression nut 1515. The compression nut 1515 likewise has external threads 1550 that engage the internal threads 1545 of the coupling element 1505. Some embodiments, such as that depicted in FIG. 21A, provide that the compression nut 1515 includes an upper flange 1555, or other radially projecting member about a perimeter of the compression nut 1515, that is configured to provide a portion of the locking mechanism between the compression nut 1515 and the coupling element 1505.

FIG. 21B illustrates a close-up view of a portion of FIG. 21A. As shown in FIG. 21B, the coupling element 1505 can include a recess 1560 along a top portion of the coupling element 1505. In some embodiments, the recess 1560 has a greater cross-sectional dimension between the laterally opposed upwardly extending projections 1540 than any internal cross-sectional dimension of the internal threads 1545. Some embodiments provide that the recess 1560 is situated on top of the internal threads 1545, such that engagement between the external threads 1550 of the compression nut 1515 and the internal threads 1545 of the coupling element 1505 is substantially beneath, or distal to, the top of the coupling element 1505, or the end into which the compression nut 1515 is received.

The recess 1516 is preferably bounded on the bottom by the internal threads 1545 and on the top by a retention member 1565, or lip. The retention member 1565 defines an annular, or semi-annular, engaging surface 1570 that, in some embodiments, defines an upper bound of the recess 1516. Some embodiments provide an angled slope 1575, or tapered portion on the retention member 1565, or lip, that extends between the engaging surface 1570 and an outer surface of the coupling element 1505. This angled slope, or tapered portion 1575, can provide a transition member that engages a portion of the compression nut 1515, as the compression nut 1515 is rotatingly inserted into the coupling element 1505. As the compression nut 1515 presses against the transition member, the rotating force that drives the compression nut 1515 downward into the coupling element 1505 is translated into a radial force that splays the laterally opposed upwardly extending projections 1540, causing the projections 1540 to deflect or move apart from each other.

The flange member 1555 of the compression nut 1515 can include a beveled, sloped, or tapered surface 1580 that constitutes a second transition member. Some embodiments provide that the beveled surface 1580 can engage the angled slope, or tapered, portion 1575 of the coupling element 1505 as the compression nut 1515 is rotated into the coupling element 1505. Accordingly, as the compression nut 1550 is received downward into the coupling element 1505, the beveled surface 1580 of the compression nut 1515 and the angled portion 1575 of the coupling element 1505 slide relative to each other and translate a radial force against the two projections 1540, causing them to deflect from one another. The deflection of 1540 is preferably substantially within an elastic range of deformation for the material of the coupling element 1505.

The flange member 1555 is preferably configured to have a height that can be fully received within the recess 1560 of the coupling element 1505, such that a flange top surface 1585 can be received into the recess 1560 and engage the engaging surface 1570 of the retention member 1565. Additionally, a cross-sectional dimension of the flange member 1555 is preferably greater than any cross-sectional dimension of the compression nut external threads 1550.

Figures 22A, 22B:
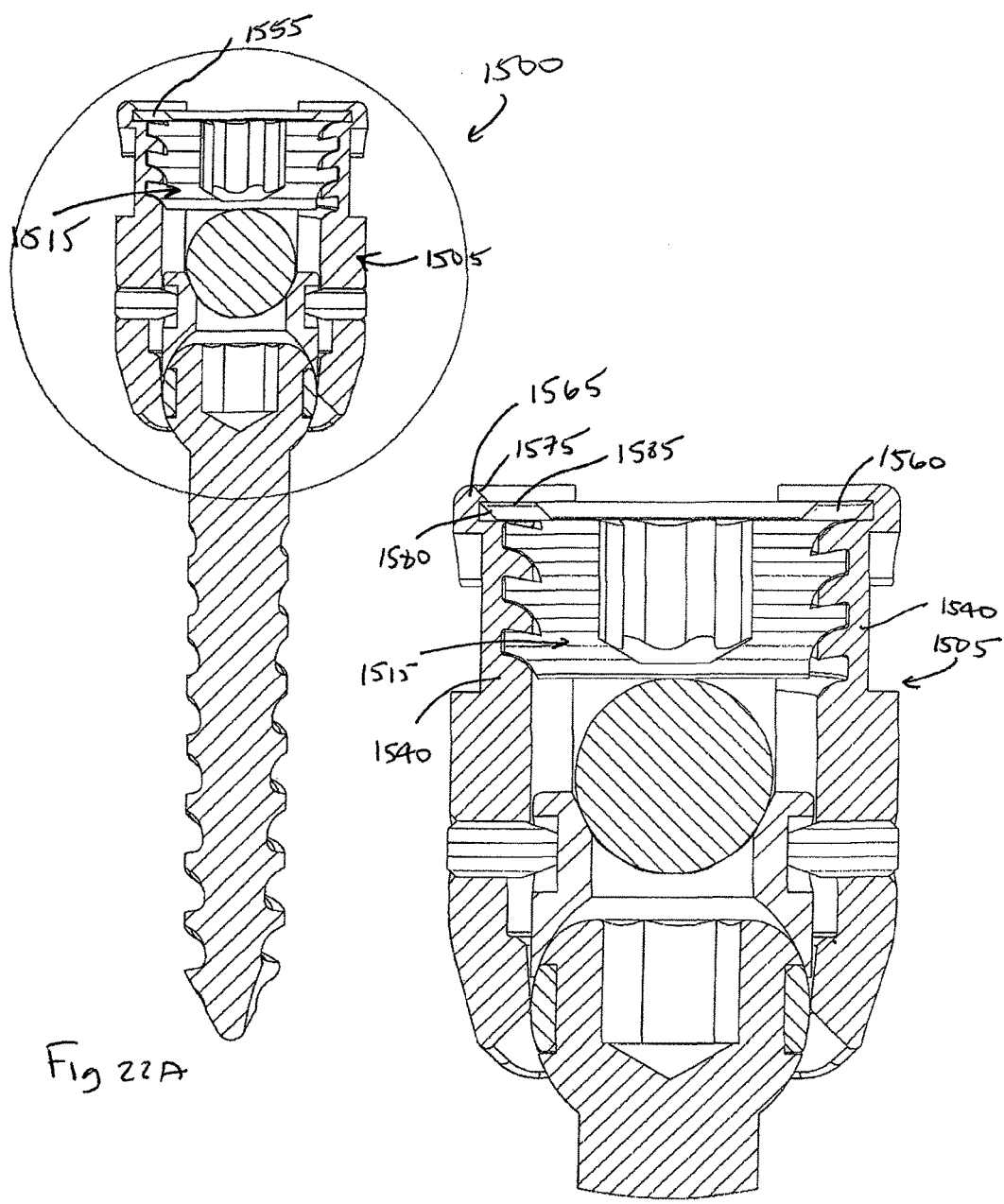
FIG. 22A is a cross-sectional exploded view of embodiments of an anchor assembly described herein.
FIG. 22B is a cross sectional exploded view of the anchor assembly depicted in FIG. 22A.

FIGS. 22A-B illustrates a cross-sectional views of embodiments of the anchor 1500, in which the compression nut 1515 has been received into the coupling element 1505. As the compression nut 1515 is received into the coupling element 1505, the upwardly extending projections 1540 will deflect as the beveled surface 1580 slides relative to the angled slope 1575. Some embodiments provide that the upwardly extending projections 1540 do not deflect away from each other more than the height of the internal threads 1545 in order to reduce the likelihood of slippage between the compression nut external threads 1550 and the coupling element internal threads 1545. When the compression nut 1515 has been received into the coupling element 1505 to the point at which the flange member 1555 is fully received within the recess 1560, the retention member, or lip 1565, is permitted to slide over the flange top surface 1585. When this happens, the substantially elastic deformation of the upwardly extending projections 1540 permits, the projections 1540 to retract toward one another such that the engaging surface 1570 rests over the flange top surface 1585, thereby substantially blocking retraction of the compression nut 1515 from the coupling element 1505.

In this configuration, the lip 1565 interlocks with the flange member 1555 to substantially prevent withdrawal of the compression nut 1515 from the coupling element 1505. Additionally, rotational movement between the compression nut 1515 and the coupling element 1505 is limited in both directions of rotation. For example, rotational movement that would drive the compression nut 1515 further into the coupling element 1505 is limited either by engagement of the flange 1555 with the internal threads 1545, or engagement of the compression nut 1515, directly or indirectly against the rod 1530, as shown in FIG. 22B. Likewise, rotational movement that would withdraw the compression nut 1515 from the coupling element 1505 is limited by engagement between the engaging surface 1570 and the flange top surface 1585.

The coupling nut 1515 can be removed from the coupling element 1505 by deflecting the upwardly extending projections 1540 from each other, thereby reducing or preventing contact between the engaging surface 1570 and the flange top surface 1585.

Figure 23:
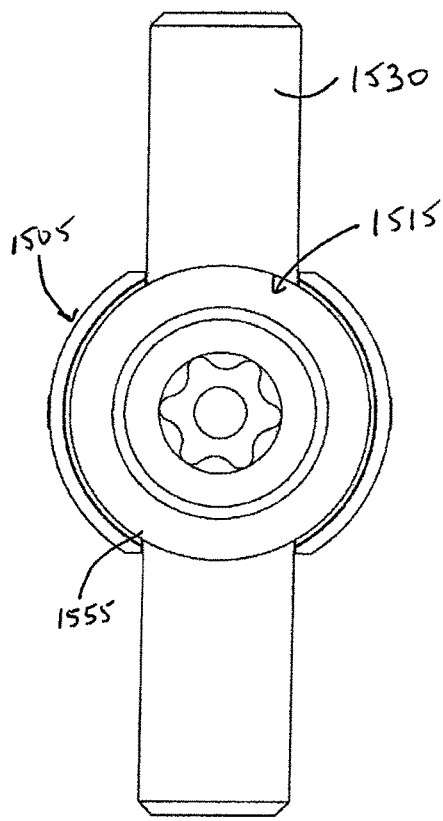
FIG. 23 is a top view of embodiments of an anchor assembly described herein.
Figure 24:
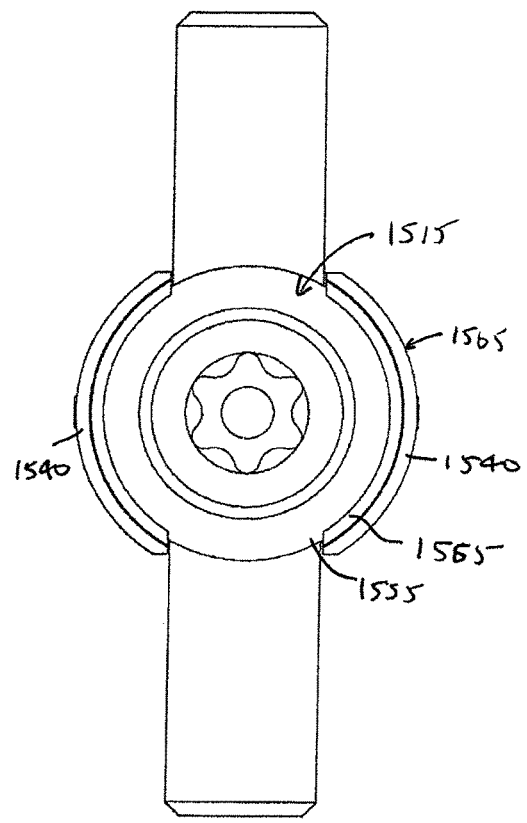
FIG. 24 is a top view of embodiments of an anchor assembly described herein.

FIGS. 23 and 24 illustrates top views of embodiments of the anchor assembly showing the coupling element 1505, compression nut 1515, and rod 1530. FIG. 23 illustrates the top view when the compression nut 1515 has not been entirely rotatingly received into the coupling element 1505. As can be seen, the retention member 1565 extends underneath a portion of the compression nut 1515. In contrast, FIG. 24 illustrates the top view after the laterally opposed upwardly extending projections 1540 have been deflected relative to each other and the flange member 1555 has been received into the recess 1560 of the coupling element 1505. Accordingly, the upwardly extending projections 1540 are shown substantially in their original orientation (following elastic deformation during deflection) with the retention member, or lip 1565, extending over a portion of the flange member 1555. In this configuration, the retention member's 1565 engage a portion of the compression nut 1515 and substantially prevent withdrawal of the compression nut 1515 from the coupling element 1505. In order for the compression nut 1515 to be removed from the coupling element 1505, the upwardly extending projections 1540 are once again be deflected from each other to allow the flange member 1555 to be free of the retention member, or lip 1565.

Figure 25:
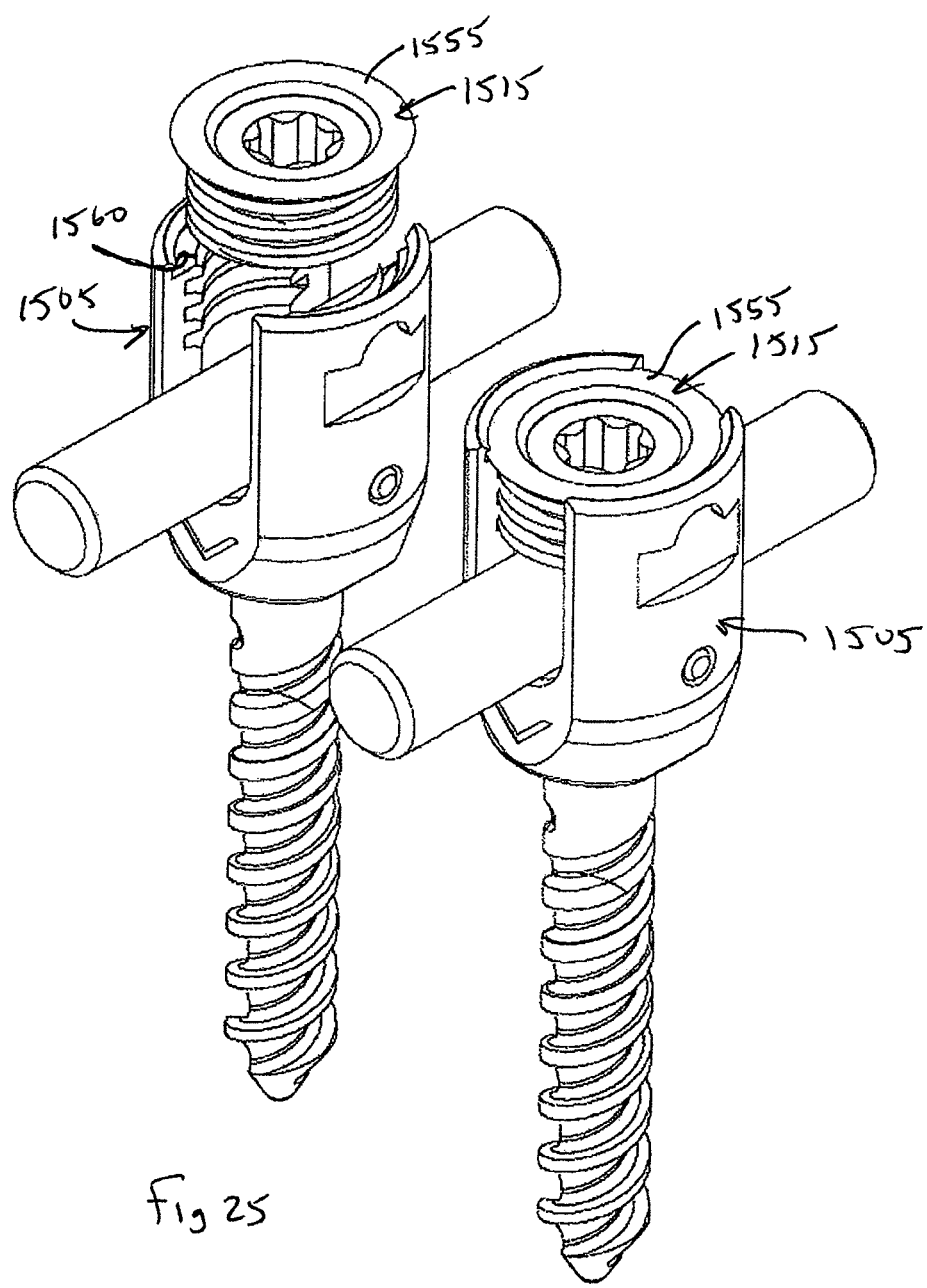
FIG. 25 are perspective views of embodiments of an anchor assemblies described herein.

FIG. 25 illustrates a perspective views of embodiments of the anchor assemblies described above. On the left, the compression nut 1515 has not yet been received by the coupling element 1505. On the right, the compression nut 1515 has been received by the coupling element 1505 such that the flange member 1555 of the compression nut 1515 extends into the recess 1560 of the coupling element 1505. In this configuration, rotational movement of the compression nut 1515 relative to the coupling element 1505 is limited to prevent withdrawal of the compression nut 1515 from the coupling element 1505.

Some embodiments of the compression nut 1515 and the coupling element 1505 can be configured to provide a locking member in additional or alternative ways. For example, FIGS. 26A-B illustrates embodiments of a coupling element 1505 and a compression nut 1515 that engage each other, for substantially locking or limiting relative rotational movement between the compression nut 1515 and the coupling element 1505, along radially facing surfaces.

Figures 26A, 26B:
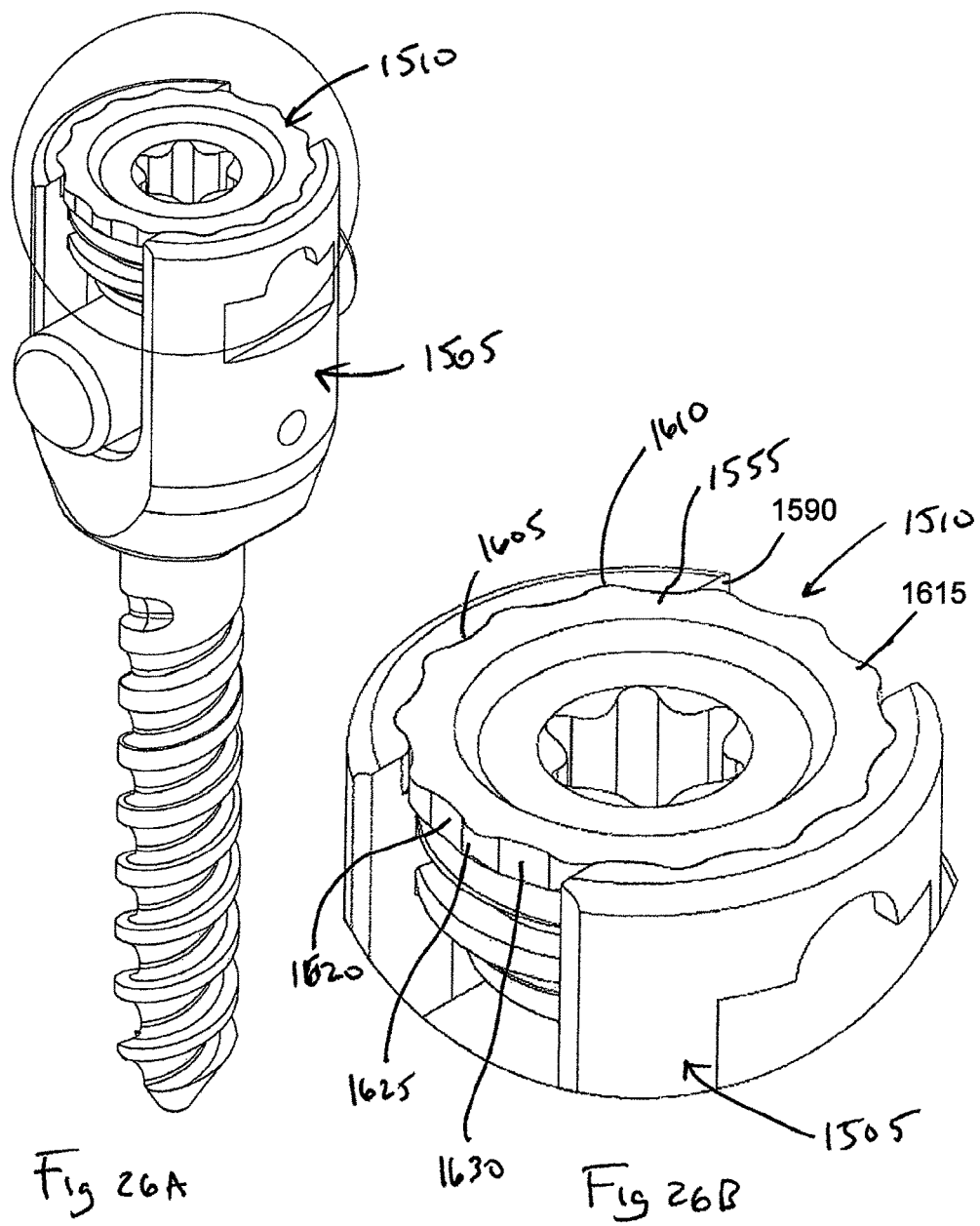
FIG. 26A is a perspective view of embodiments of an anchor assembly described herein.
FIG. 26B is a perspective view of the anchor assembly depicted in FIG. 26A.

Depicted in FIGS. 26A-B are embodiments of a coupling element 1505 have any retention member 1565 that has a coupling element radially facing contact surface 1590. In some embodiments, a coupling element radially facing contact surface 1590 can have a scalloped profile that defines internal scalloped edges having troughs 1605 and crests 1610 that extend substantially along the access of the anchor 1500. In some embodiments, the scalloped edges with troughs and crests can be one or more protrusions or recesses along an inner surface of the coupling member 1505.

Some embodiments provide a compression nut 1515 that has a flange 1615 with a radially outward facing surface 1620 having a scalloped profile, a series of detents 1625 and channels 1630, and/or one or more protrusions or recesses. A radially outward facing surface 1620 of the compression nut 1515 is configured to engage the coupling element radially facing contact surface 1590 to provide a locking mechanism that limits relative rotation between the coupling element 1505 and the compression nut 1515. In some embodiments, the coupling element 1505 and the compression nut 1515 can provide a series of engaging members that are interlocked or provide an interference fit upon relative rotation of the compression nut 1515 and the coupling element 1505. Accordingly, when the compression nut 1515 is received into the coupling element 1505 by rotatingly engaging the threads of the compression nut 1515 with those of the coupling element 1505, such that the radially outward facing surface 1620 of the compression nut 1515 engages the coupling element radially facing contact surface 1590, further relative rotation between the compression nut 1515 and the coupling element 1505 is prevented unless the laterally opposed upwardly extending projections 1540 deflect from, or bow out relative to, each other.

A degree of locking force provided by the engaging surfaces 1590, 1620 can be adjusted by modifying the material from which the coupling element 1505 is manufactured. Additionally, the degree of locking force, required to either rotate the compression nut 1515 in a tightening or loosening fashion, can be adjusted by modifying the interlocking, interfering, or engaging surfaces of the compression nut 1515 and the coupling element 1505. For example, surfaces have been deeper troughs or higher crests, deeper recesses or longer protrusions, can provide a higher degree of locking force because the laterally opposed upwardly extending projections 1540, would need to deflect farther from each other.

Figures 27A, 27B:
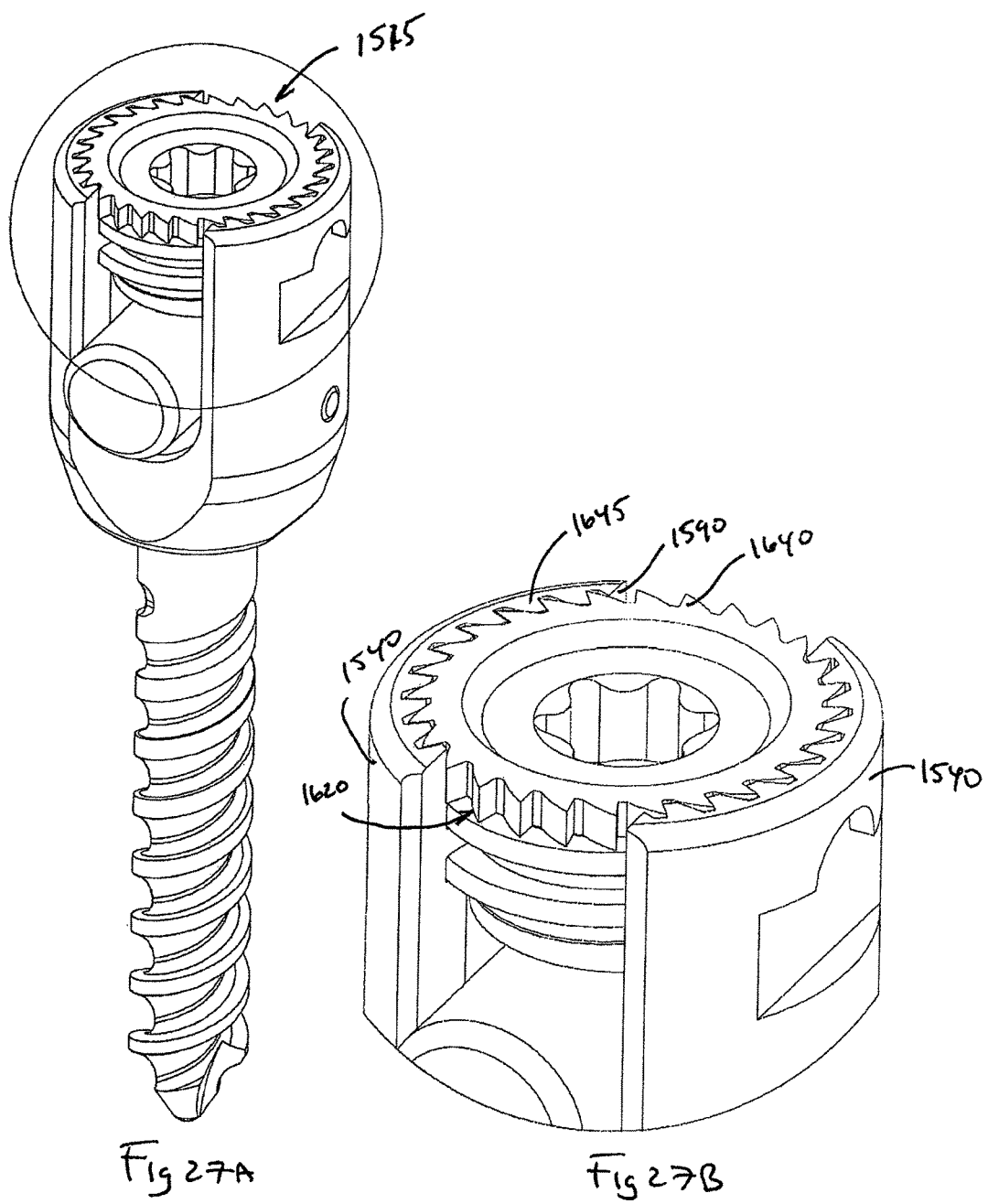
FIG. 27A is a perspective view of embodiments of an anchor assembly described herein.
FIG. 27B is a perspective view of the anchor assembly depicted in FIG. 27A.

FIGS. 27A-B illustrate embodiments of the radially outward facing surface 1620 of the compression nut 1515, and the coupling element radially facing contact surface 1590, having protrusions and recesses in an interlocking sawtooth arrangement. In these embodiments, the sawtooth projections 1640 of the compression nut 1515 interlock with the sawtooth protrusions 1645 of the coupling element 1505. The buttressed, or undercut, configuration of the sawtooth arrangement can provide additional locking security against relative rotation between the compression nut 1515 and the coupling element 1505 that might permit withdrawal of the compression nut 1515 from the coupling element 1505.

In order for the compression nut 1515 to be removed from the coupling element 1505, the laterally opposed upwardly extending projections 1540 must be deflected to disengage the interlocking sawtooth arrangement between the sawtooth projections 1640 and the sawtooth protrusions 1645. A tool can be used in connection with the anchors 1500 of this disclosure to facilitate deflection between the laterally opposed upwardly extending projections 1540 in order to release the compression nut 1515 from engagement with the coupling element 1505 so the coupling nut 1515 can be removed. Although projections and protrusions are used to address different structures in this disclosure, with respect to the embodiments described in FIGS. 27A-B, these terms are intended to be used interchangeably.

The sawtooth arrangement between the sawtooth projections 1640 and the sawtooth protrusions 1645 are preferably configured to have angulated surfaces that will permit relative rotation between the coupling element 1505 in the compression nut 1515 as the compression nut 1515 is rotatingly received into, or threaded into, the coupling element 1505. Upon each ratchet of rotation, the laterally opposed upwardly extending projections 1540 deflect outward relative to each other to permit the sawtooth projections 1640 to slide against the sawtooth protrusions 1645. Once the sawtooth projections 1640 aligns with recesses 1650, or the spaces between the sawtooth protrusions 1645, the laterally opposed upwardly extending projections 1540 are permitted to retract back toward each other, thereby providing an interlocking engagement between the compression nut 1515 and the coupling element 1505.

Figure 28:
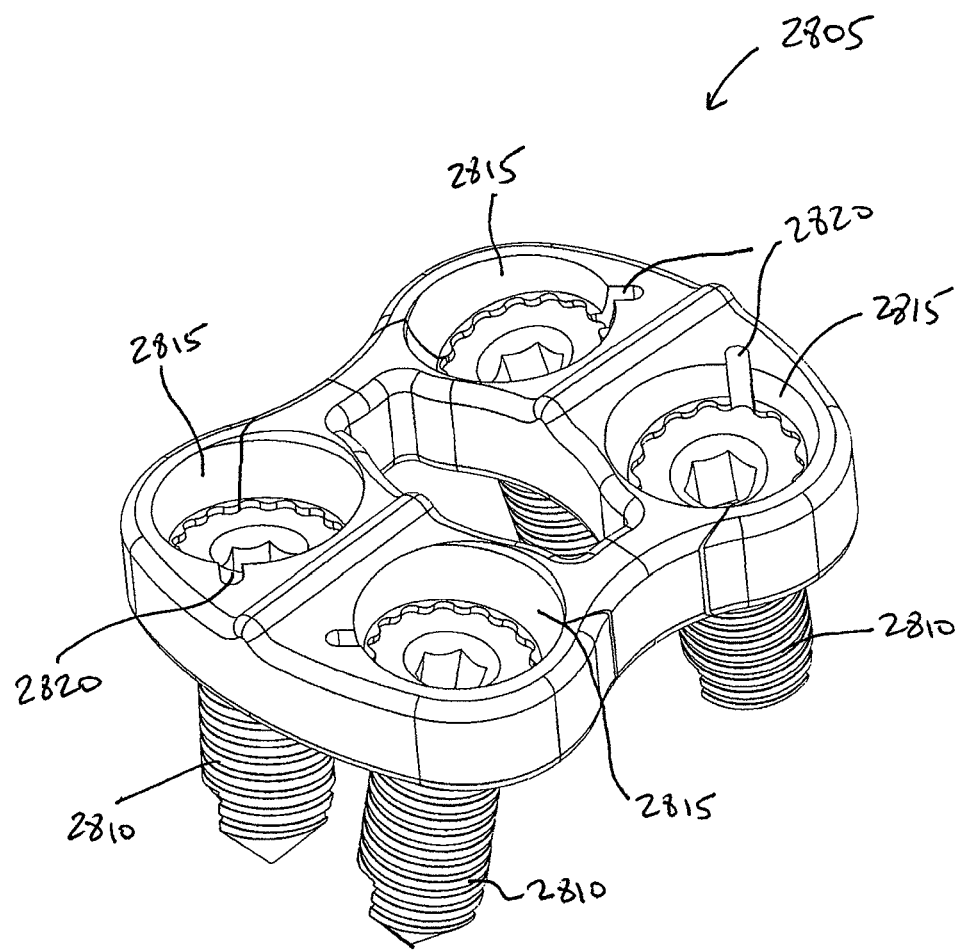
FIGS. 28-30 show additional embodiments.

FIG. 28 shows another embodiment of a device that employs the configurations described above with respect to FIG. 26a and FIG. 26B. The device is a orthopedic plate, such as an anterior cervical plate 2805. The plate 2805 has a plurality of anchors 2810 that extend through openings 2815 in the plate 2805. The anchors 2810 have heads that employ the scalloped profile that defines internal scalloped edges having troughs and crests that extend substantially along the outer edge of the anchor head, such as in a manner described above with reference to FIGS. 26A and 26B. The troughs and crests interface with a series of troughs and crests around the openings 2815 of the plate 2805. Each of the openings 2815 includes an outwardly extending slot 2820 that permits the opening 2815 to expand and contract outward as the head of the anchor is rotated. This enables an anti-backout feature that prevents or substantially inhibits undesired rotation and backout of the anchors.

Figure 29:
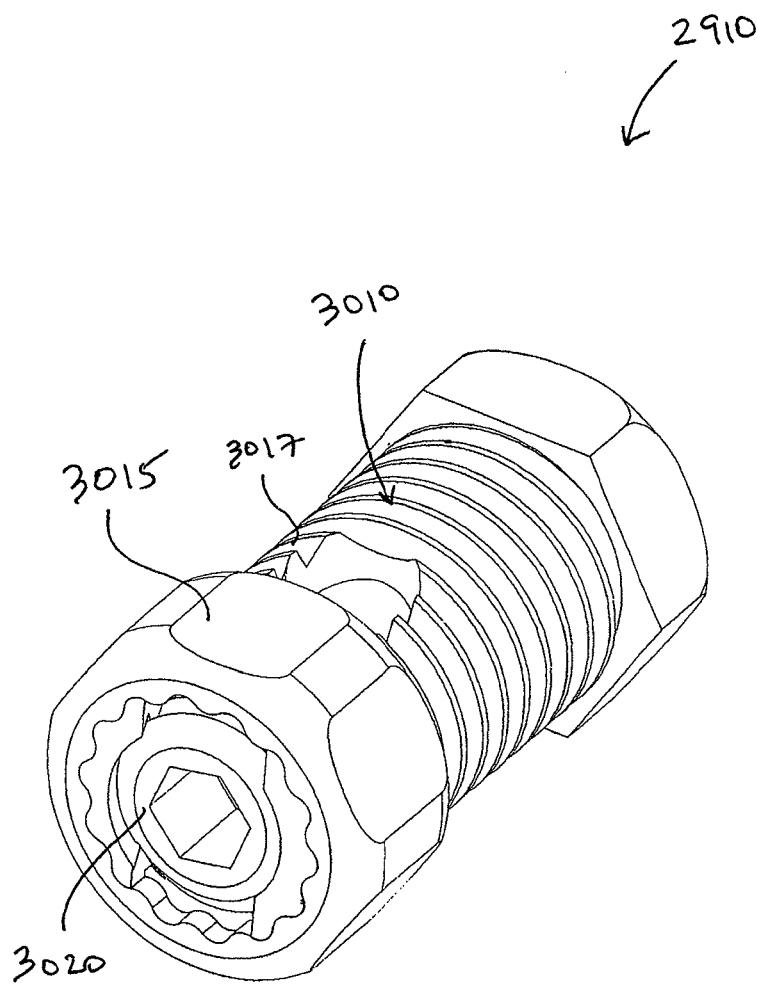
Figure 30:
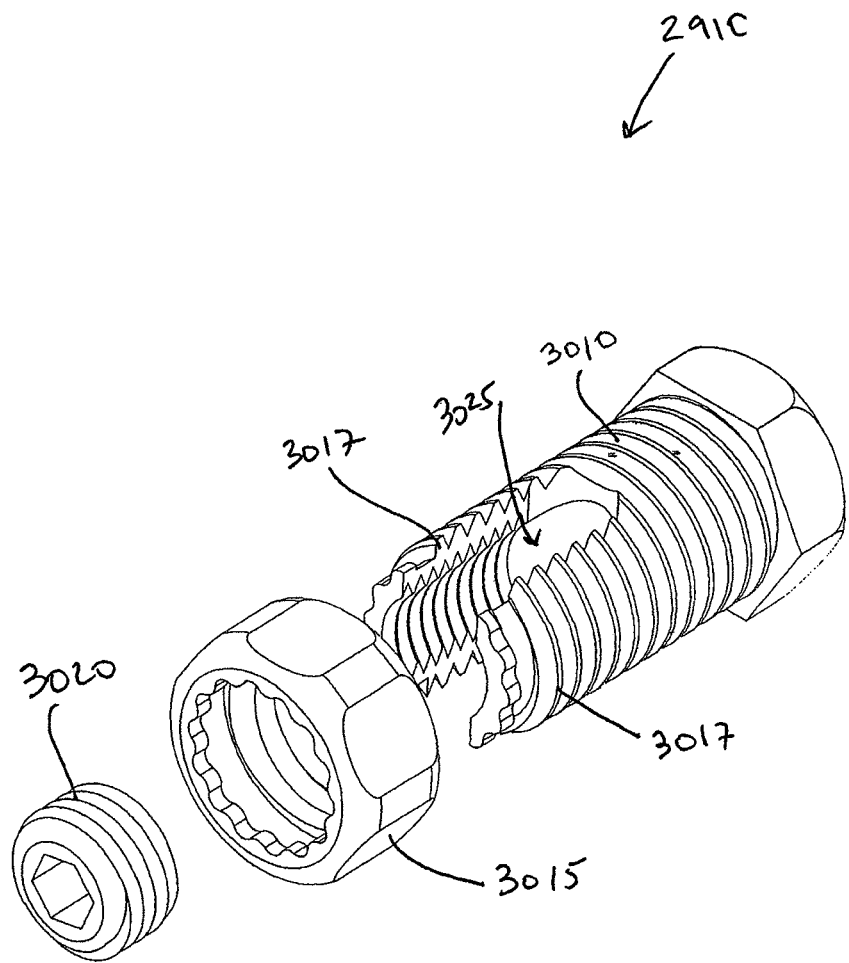

FIG. 29 shows an embodiment of a bushing 2910 that also employs an antibackout feature such as described above. As shown in the exploded view of FIG. 30, the bushing includes a bolt 3010 having an internal bore and a slot 3025 that permits a pair wings 3017 to flex inward an outward. A nut 3015 has internal threads and an internal edge with troughs and crests interface with a series of troughs and crests on the wings 2017. This enables the anti-backout feature as described above. A lock screw 3020 has external threads that can be threaded into the bore of the bolt 3010 for locking the system.

In some embodiments, the various components of the assembly are manufactured of an inert material, such as, for example, stainless steel or titanium.

The various embodiments of top saddles, compression nut threading geometries, and coupling element threading geometries are described herein with respect to polyaxial pedicle screws. However, it should be appreciated that they can be used with monoaxial pedicle screws as well. The devices and concepts described herein may be used in devices for any of a variety of industries and/or products, including aerospace, orthopedic implants, manufacturing, machinery, automotive, marine, military, and/or any industries that deal with vibration and cyclic loads and that may use an anti-vibration/anti loosening locking assembly to prevent failures and decrease maintenance cost.

The description of the disclosure is provided to enable any person skilled in the art to practice the various embodiments described herein. While the embodiments have been particularly described with reference to the various figures and disclosure, it should be understood that these are for illustration purposes only and should not be taken as limiting the scope of the disclosure.

There may be many other ways to implement the embodiments. Various functions and elements described herein may be partitioned differently from those shown without departing from the spirit and scope of the disclosure. Various modifications to these embodiments will be readily apparent to those skilled in the art, and generic principles defined herein may be applied to other embodiments. Thus, many changes and modifications may be made to embodiments, by one having ordinary skill in the art, without departing from the spirit and scope of the disclosure.

A reference to an element in the singular is not intended to mean "one and only one" unless specifically stated, but rather "one or more." The term "some" refers to one or more. Any headings and subheadings are used for convenience only, do not limit the disclosure, and are not referred to in connection with the interpretation of the description of the disclosure. All structural and functional equivalents to the elements of the various embodiments described throughout this disclosure that are known or later come to be known to those of ordinary skill in the art are expressly incorporated herein by reference and intended to be encompassed by the disclosure. Moreover, nothing disclosed herein is intended to be dedicated to the public regardless of whether such disclosure is explicitly recited in the above description.

The invention claimed is:
1. A bone stabilizer assembly, comprising:
 (a) a fixation member configured to engage a bone and having a head portion and a shank portion;
 (b) a coupling member having:
  (i) two opposed arms separated by an internal bore sized to receive the shank portion of the fixation member, the internal bore having two opposed threaded internal surfaces;
  (ii) a seat configured to support the head portion of the fixation member; and
  (iii) a locking member first portion;
 (c) a compression nut configured to be rotatingly received by the coupling member and to threadingly engage the threaded internal surfaces, the compression nut having:
  (i) a locking member second portion, the compression nut configured to translate a force to the head portion through the rod such that the head portion is forced against the seat of the coupling member to limit relative movement between the fixation member and the coupling member;
 wherein the coupling member and the compression nut are configured to engage each other via the locking member first and second portions such that relative rotation between the coupling member and compression nut is limited unless the two arms are caused to splay apart by an interaction of the locking member first portion and the locking member second portion; and
 wherein the locking member first and second portions comprise sawtooth edges that interlock to limit relative rotational movement between the compression nut and the coupling member without deflection of the two opposed threaded internal surfaces.

2. The assembly of claim 1, wherein the locking member first portion comprises a recess in the internal bore, the recess having a greater cross-sectional dimension than a greatest cross-sectional dimension of the threaded internal surfaces.

3. The assembly of claim 2, wherein the locking member first portion comprises a lip having a cross-sectional dimension less than the cross-sectional dimension of the recess, and the locking member second portion is configured to engage the lip and thereby deflect the two opposed threaded internal surfaces relative to each other as the compression nut is received by the coupling member.

4. The assembly of claim 1, wherein the locking member second portion comprises a flange on the compression nut, the flange having a greater cross-sectional dimension than a greatest cross-section dimension of the threaded internal surfaces of the coupling member.

5. The assembly of claim 4, wherein the locking member first portion comprises a lip that interlocks with a portion of the flange to prevent withdrawal of the compression nut from the coupling member.

6. The assembly of claim 1, wherein the locking member first and second portions comprise a plurality of detents that limit relative rotation between the compression nut and the coupling member.

7. A coupling member assembly, for securing a pedicle screw to a retention rod, the assembly comprising:
 (a) a coupling member having two opposed arms, two threaded internal surfaces, and a locking member first portion; and
 (b) a compression nut configured to be received by the coupling member and to threadingly engage the coupling member threaded internal surfaces, the compression nut having a locking member second portion;
 wherein the coupling member and the compression nut are configured to engage each other via the locking member first and second portions such that relative rotation between the coupling member and compression nut is limited unless the two arms are caused to splay apart by an interaction of the locking member first portion and the locking member second portion ; and
 wherein the locking member first and second portions comprise sawtooth edges that interlock to limit relative rotational movement between the compression nut and the coupling member without deflection of the two opposed threaded internal surfaces.

8. The assembly of claim 7, wherein the locking member first portion comprises a recess in the internal bore, the recess having a greater cross-sectional dimension than a greatest cross-sectional dimension of the threaded internal surfaces.

9. The assembly of claim 8, wherein the locking member first portion comprises a lip having a cross-sectional dimension less than the cross-sectional dimension of the recess, and the locking member second portion is configured to engage the lip and thereby deflect the two opposed threaded internal surfaces relative to each other as the compression nut is received by the coupling member.

10. The assembly of claim 7, wherein the locking member second portion comprises a flange on the compression nut, the flange having a greater cross-sectional dimension than a greatest cross-section dimension of the threaded internal surfaces of the coupling member.

11. The assembly of claim 10, wherein the locking member first portion comprises a lip that interlocks with a portion of the flange to prevent withdrawal of the compression nut from the coupling member.

12. The assembly of claim 7, wherein the locking member first and second portions comprise a plurality of detents that limit relative rotation between the compression nut and the coupling member.

* * * * *